(12) United States Patent
Hiraide et al.

(10) Patent No.: US 10,601,436 B2
(45) Date of Patent: Mar. 24, 2020

(54) SUCCESSIVE APPROXIMATION A/D CONVERTER, IMAGING DEVICE, ENDOSCOPE, AND SETTING METHOD

(71) Applicant: OLYMPUS CORPORATION, Tokyo (JP)

(72) Inventors: Shuzo Hiraide, Tokyo (JP); Yasunari Harada, Ebina (JP); Masato Osawa, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 16/415,067

(22) Filed: May 17, 2019

(65) Prior Publication Data

US 2019/0280707 A1 Sep. 12, 2019

Related U.S. Application Data

(63) Continuation of application No. PCT/JP2017/032169, filed on Sep. 6, 2017.

(30) Foreign Application Priority Data

Dec. 21, 2016 (JP) ................................ 2016-247964

(51) Int. Cl.
*H03M 1/34* (2006.01)
*H03M 1/38* (2006.01)
(Continued)

(52) U.S. Cl.
CPC ............... *H03M 1/38* (2013.01); *A61B 1/045* (2013.01); *H03M 1/10* (2013.01); *H04N 5/378* (2013.01); *H03M 1/802* (2013.01)

(58) Field of Classification Search
CPC .......... H03M 1/38; H03M 1/10; H03M 1/802; H03M 1/12; H03M 1/00; A61B 1/045; H04N 5/378

(Continued)

(56) References Cited

U.S. PATENT DOCUMENTS 4,200,863 A * 4/1980 Hodges ................... H03M 1/38
341/156
6,404,376 B1 6/2002 Kalthoff et al.
(Continued)

FOREIGN PATENT DOCUMENTS

| JP | 2003-504912 A | 2/2003 |
| JP | 2013-526179 A | 6/2013 |
| WO | WO 2016/170642 A1 | 10/2016 |

OTHER PUBLICATIONS

International Search Report dated Nov. 28, 2017 issued in PCT/JP2017/032169.

(Continued)

*Primary Examiner* — Jean B Jeanglaude
(74) *Attorney, Agent, or Firm* — Scully, Scott, Murphy & Presser, P.C.

(57) ABSTRACT

A disclosed analog-to-digital converter includes; a sampling circuit to sample a pair of analog signals as a differential input signal; a binary capacitance holding the sampled pair of analog signals and reflecting a level of a reference signal to the analog signals through the binary capacitance to generate a pair of voltage signals; a comparator including a transistor to which the voltage signals are input, to compare one of the voltage signals with the other; a correction circuit provided previously to the comparator, to output to the comparator the pair of voltage signals in which voltage dependency of stray capacitance in the input transistor is cancelled; and a controller that successively determines a value of each bit of a digital signal corresponding to the binary capacitance based on a comparison by the comparison circuit, and reflects the value of each bit of the digital signal to the reference signal.

9 Claims, 19 Drawing Sheets

(51) Int. Cl.
*A61B 1/045* (2006.01)
*H04N 5/378* (2011.01)
*H03M 1/10* (2006.01)
*H03M 1/80* (2006.01)

(58) Field of Classification Search
USPC .................................... 341/158, 155, 161
See application file for complete search history.

(56) References Cited

U.S. PATENT DOCUMENTS

| | | | |
|---|---|---|---|
| 8,059,020 B2* | 11/2011 | Schatzberger | H03M 1/185 |
| | | | 341/138 |
| 9,467,159 B1* | 10/2016 | Tai | H03M 1/1057 |
| 9,654,132 B2* | 5/2017 | Venca | H03M 1/667 |
| 2011/0260899 A1 | 10/2011 | Snedeker | |
| 2013/0147349 A1* | 6/2013 | Li | H01J 61/54 |
| | | | 315/34 |
| 2013/0162454 A1* | 6/2013 | Lin | H03M 1/38 |
| | | | 341/120 |
| 2014/0247177 A1* | 9/2014 | Draxelmayr | H03M 1/0692 |
| | | | 341/156 |

OTHER PUBLICATIONS

Harpe P.J.A. et al., "A 26 μW 8 bit 10 MS/s Asynchronous SAR ADC for Low Energy Radios", IEEE Journal of Solid-State Circuits, vol. 46, No. 7, Jul. 2011, pp. 1585-1595, cited in spec on p. 1.

* cited by examiner

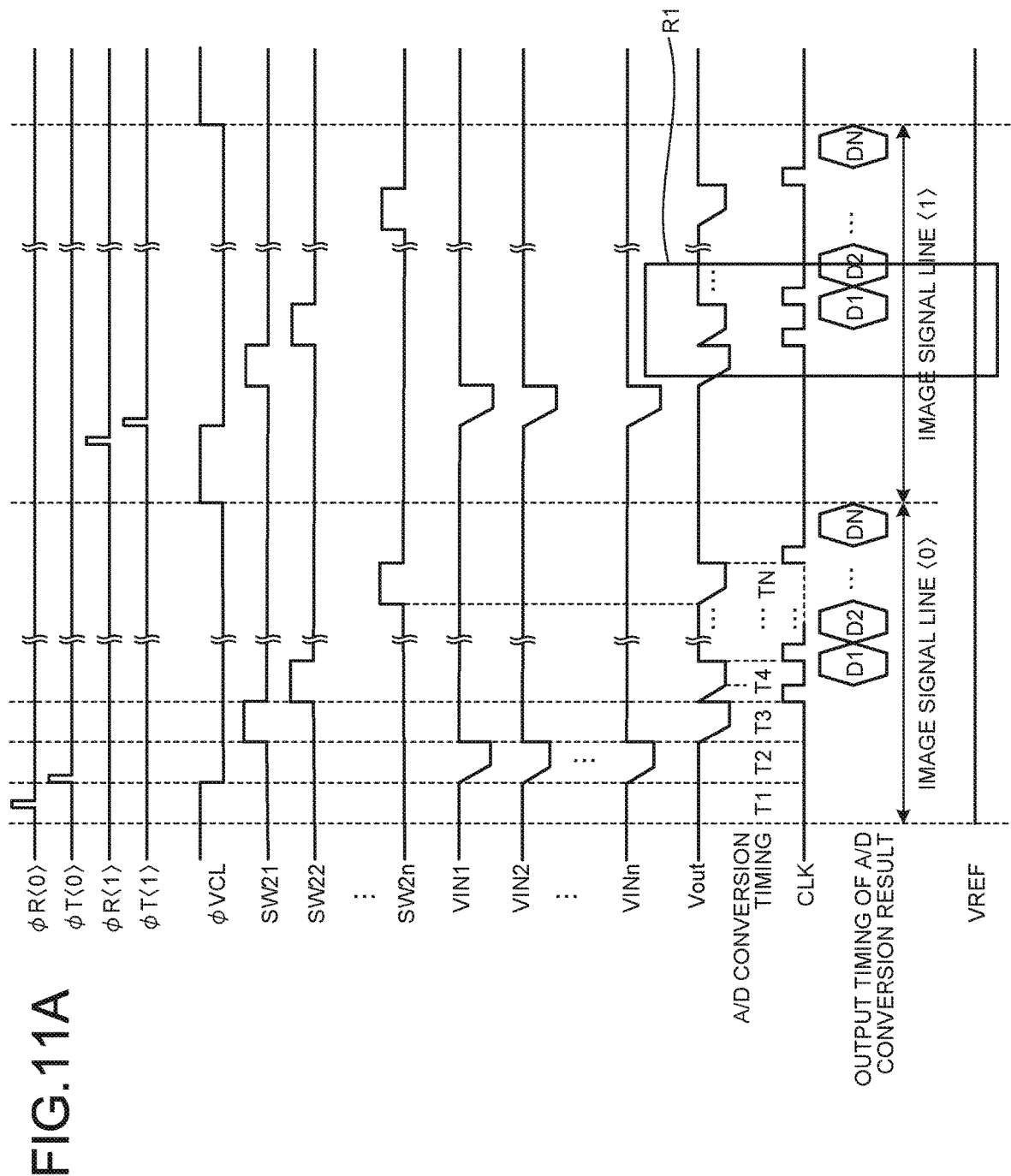

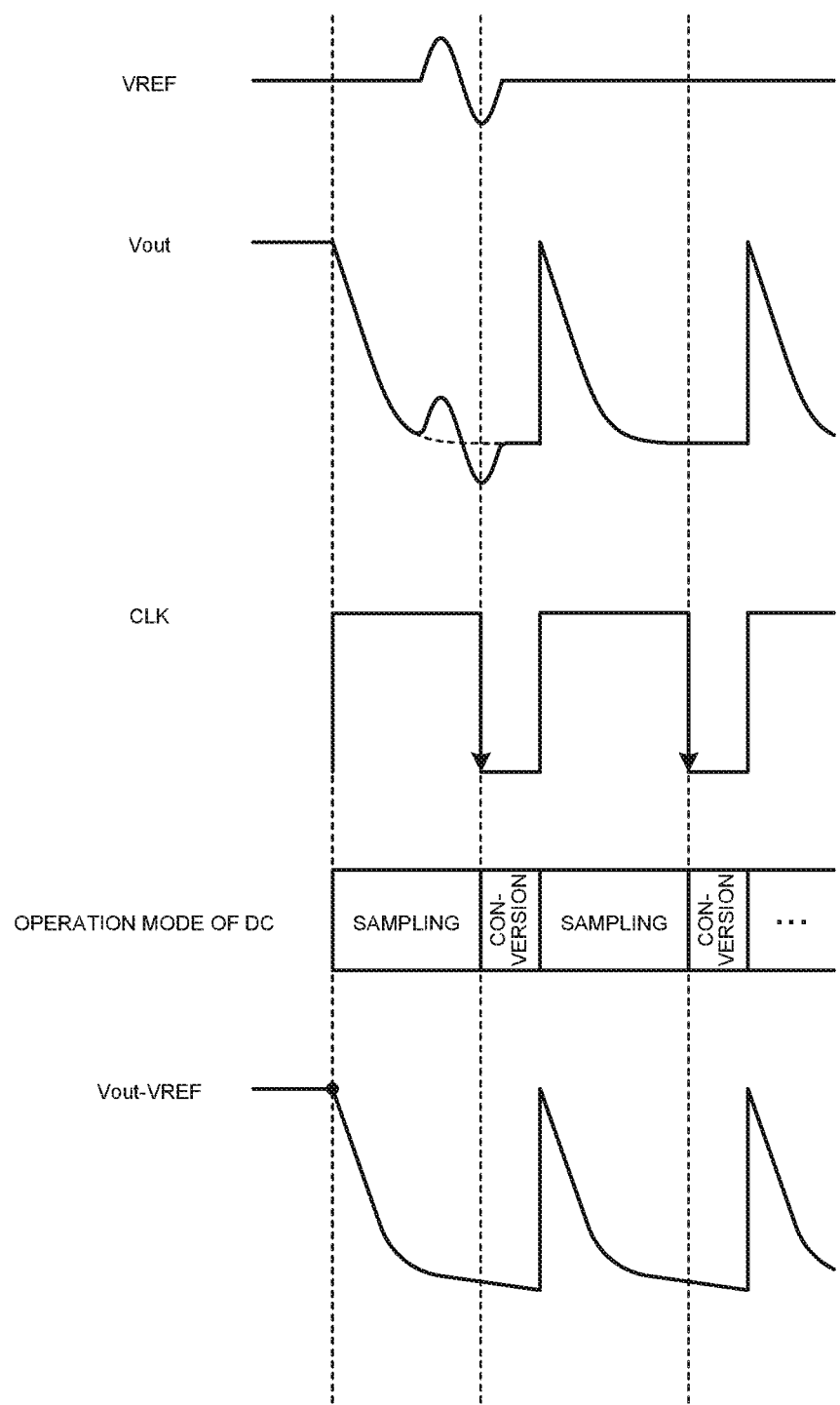

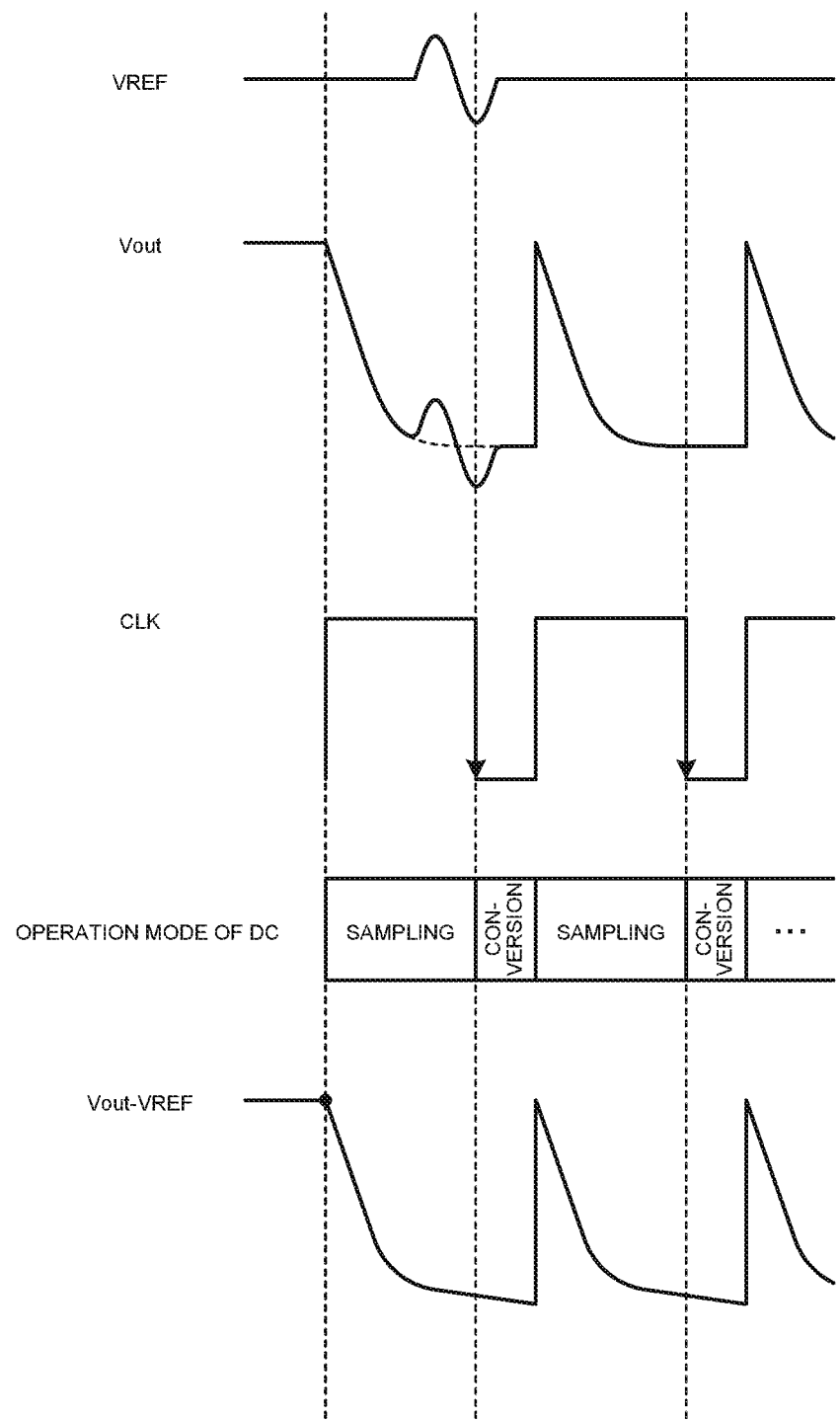

SUCCESSIVE APPROXIMATION A/D CONVERTER, IMAGING DEVICE, ENDOSCOPE, AND SETTING METHOD

CROSS-REFERENCE TO RELATED APPLICATION

This application is a continuation of PCT International Application No. PCT/JP2017/032169 filed on Sep. 6, 2017, which designates the United States, incorporated herein by reference, and which claims the benefit of priority from Japanese Patent Application No. 2016-247964, filed on Dec. 21, 2016, incorporated herein by reference.

BACKGROUND

The present disclosure relates to a successive approximation analog-to-digital (A/D) converter configured to convert an analog signal, which is externally input, into a digital signal, an imaging device, an endoscope, and a setting method.

As a low power consumption analog-to-digital (A/D) converter, a differential input asynchronous successive approximation A/D converter has been known (for example, in "A 26 µW 8 bit 10 MS/s Asynchronous SAR ADC for Low Energy Radios", *IEEE JOURNAL OF SOLID-STATE CIRCUITS*, Vol. 46, No. 7, pp. 1585-1596, July 2011). This successive approximation A/D converter holds a pair of analog signals input in a sample hold circuit as a differential input signal, and causes comparison circuit to generate a comparison voltage signal by reflecting a reference signal in the held analog signals through a capacitor circuit. Based on this comparison voltage signal, a successive-approximation logical circuit determines respective bit values (0 or 1) of MSB to LSB of the digital signal corresponding to the differential input signal according to a binary search algorithm, and feeds back the determined respective bit values to the reference signal.

The successive approximation A/D converter can be configured mostly with a digital circuit, without using an analog circuit, such as an operational amplifier. Therefore, the successive approximation A/D converter can be implemented in a small size by using a minute complementary metal oxide semiconductor (CMOS) process, and can reduce power consumption. In terms of capability of reducing power consumption and downsizing, the successive approximation A/D converter is used for a system large scale integration (LSI) of, for example, a mobile device.

SUMMARY

According to a first aspect of the present disclosure, a successive approximation analog-to-digital converter is provided which includes a sampling circuit configured to sample a pair of analog signals input as a differential input signal; a capacitor circuit that has a binary capacitance configured to hold the pair of analog signals sampled by the sampling circuit, the capacitor circuit being configured to reflect a signal level of a reference signal to the pair of analog signals through the binary capacitance to generate a pair of voltage signals; a comparator circuit that includes an input transistor to which the pair of voltage signals are input, the comparator circuit being configured to compare one of the pair of the voltage signals with the other signal of the pair of voltage signals; a correction circuit that is provided in a previous stage to the comparator circuit, the correction circuit being configured to output the pair of voltage signals in which voltage dependency of stray capacitance in the input transistor is cancelled to the comparator circuit; and a control circuit configured to successively determine a value of each bit of a digital signal corresponding to the binary capacitance based on a comparison result by the comparison circuit, and to reflect the value of each bit of the digital signal to the reference signal.

According to a second aspect of the present invention, an imaging device is provided which includes the successive approximation A/D converter according to the first aspect; an imaging device including a plurality of pixels that are arranged in a two-dimensional matrix, and that receive light input from outside to perform photoelectric conversion, and that outputs an imaging signal, wherein the imaging device includes a noise removing circuit that is arranged for each of columns of the two-dimensional matrix in which the pixels are arranged, the noise removing circuit being configured to remove a noise component included in the imaging signal; a plurality of column source-follower buffers that are arranged for each of the columns of the two-dimensional matrix in which the pixels are arranged, the plurality of column source-follower buffers being configured to and that amplify the imaging signal from which the noise component is removed by the noise removing unit; a column selecting circuit that sequentially selects the column source-follower buffers to output the imaging signal; and a buffer circuit that forms a voltage follower circuit, being connected to the column source-follower buffer sequentially selected by the column selecting circuit, and that subjects a voltage of the imaging signal output from the column source-follower buffer to impedance transformation, to output to the successive approximation analog-to-digital converter.

According to a third aspect of the present invention, an endoscope is provided which includes an imaging device according to the second aspect; and an insertion portion insertable to a subject, the insertion portion includes the imaging device at a distal end.

According to a fourth aspect of the present invention, a setting method that is performed in a successive approximation analog-to-digital converter is provided. The successive approximation analog-to-digital converter includes a correction circuit that includes a sampling circuit that samples a pair of analog signals input as a differential input signal; a capacitor circuit that has a binary capacitance holding the pair of analog signals sampled by the sampling circuit, the capacitor circuit being configured to reflect a signal level of a reference signal to the pair of analog signals through the binary capacitance to generate a pair of voltage signals; a comparator circuit that includes an input transistor to which the pair of voltage signals are input, the comparator circuit being configured to compare one of the pair of voltage signals with the other signal of the pair of voltage signals; a correction transistor that is provided in a previous stage to the comparator circuit, the correction transistor being configured to cancel voltage dependency of stray capacitance in the input transistor; and a bias circuit that applies a predetermined bias voltage to the correction transistor, the correction circuit being configured to output the pair of voltage signals to the comparator circuit; and a control circuit configured to successively determine a value of each bit of a digital signal corresponding to the binary capacitance by binary search, based on a comparison result by the comparator circuit, and to reflect the value of each bit of the digital signal to the reference signal. The method includes setting a value of the bias voltage applied by the bias circuit; applying the bias voltage having the set value sequentially to the correction transistor; inputting a test signal to the successive approximation A/D converter sequentially such that the successive approximation A/D converter is caused to perform A/D conversion; calculating an integral non-linearity difference of each of the output code based on a measurement result obtained by sequentially measuring the output code converted at the A/D conversion; calculating respective maximum value and minimum value of the integral non-linearity difference for each of the output code, based on the integral non-linearity difference; and setting a value of the bias voltage such that a difference between absolute values of the calculated maximum values and the calculated minimum values is reduced, and such that an average value of the absolute values of the maximum values and the minimum values is reduced, as a value of the bias voltage to be applied by the bias circuit.

The above and other features, advantages and technical and industrial significance of this disclosure will be better understood by reading the following detailed description of presently preferred embodiments of the disclosure, when considered in connection with the accompanying drawings.

BRIEF DESCRIPTION OF THE DRAWINGS

FIG. 11A is a timing chart illustrating an operation of the imaging device according to the first embodiment of the present disclosure;

FIG. 11B is a schematic diagram in which part of the timing chart in a region R1 in FIG. 11A is enlarged;

FIG. 16B is a schematic diagram in which part of the timing chart in a region R2 in FIG. 16A is enlarged;

DETAILED DESCRIPTION OF THE PREFERRED EMBODIMENTS

An endoscope system that includes an endoscope having an imaging device at a distal end of an insertion portion to be inserted into a subject is described as a form (hereinafter, "embodiment") to implement the present disclosure. The embodiment is not intended to limit the present disclosure. Moreover, it is described giving like reference symbols to like parts throughout the drawings. Furthermore, it is noted that the drawings are of schematic illustration, and a relationship between thickness and width dimensions of respective components, a ratio of the respective components, and the like differ from those in an actual situation. Furthermore, there can be part in which relationships in dimensions or ratios differ from one another among the drawings.

First Embodiment

Configuration of Endoscope

Figure 1:
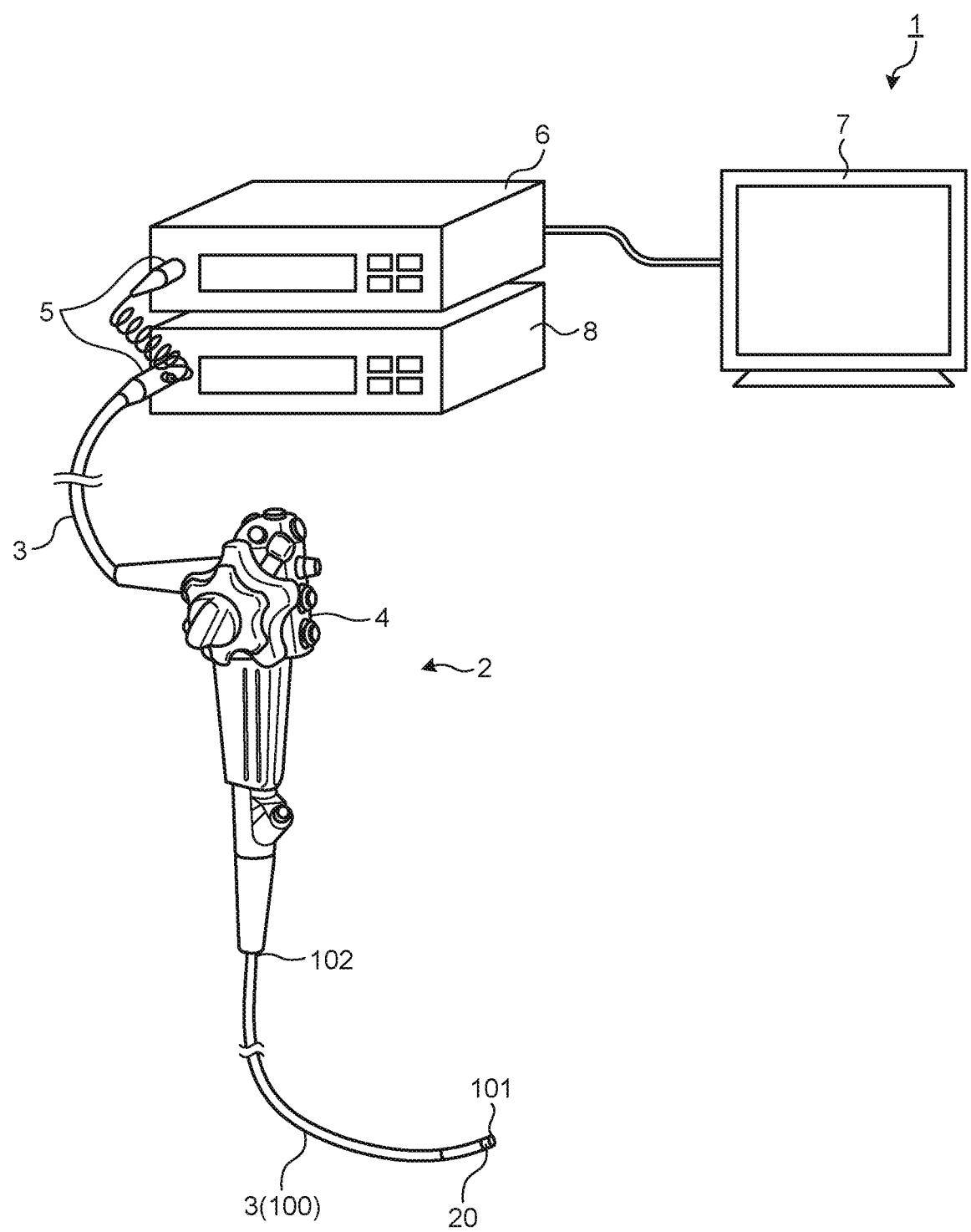
FIG. 1 is a schematic diagram schematically illustrating an entire configuration of an endoscope system according to a first embodiment of the present disclosure.

FIG. 1 is a schematic diagram schematically illustrating an entire configuration of an endoscope system according to a first embodiment of the present disclosure. An endoscope system 1 illustrated in FIG. 1 includes an endoscope 2, a transmission cable 3, a connector unit 5, a processor 6, a display device 7, and a light source device 8.

The endoscope 2 images an inside of a subject, having an insertion portion 100 that is part of the transmission cable 3 inserted into a body cavity of the subject, and outputs an imaging signal to the processor 6. Moreover, the endoscope 2 has an imaging device 20 that images an inside of the subject and generates the imaging signal. The imaging device 20 is provided at a distal end portion 101 of the insertion portion 100 that is inserted into a body cavity of a subject, which is at one end of the transmission cable 3. Furthermore, the endoscope 2 has an operation unit 4 that accepts various kinds of operations with respect to the endoscope 2. The operation unit 4 is provided at a distal end portion 102 of the insertion portion 100. The imaging signal of an internal body image imaged by the imaging device 20 is output to the connector unit 5 through the transmission cable 3 having length of, for example, several meters (m).

The transmission cable 3 connects the endoscope 2 and the connector unit 5, and connects the endoscope 2 with the processor 6 and the light source device 8. Moreover, the transmission cable 3 transmits the imaging signal generated by the imaging device 20 to the connector unit 5. The transmission cable 3 is constituted of a cable, an optical fiber, or the like.

The connector unit 5 is connected to the processor 6 and the light source device 8, and subjects the imaging signal output by the endoscope 2 connected thereto to predetermined signal processing to output to the processor 6.

The processor 6 subjects the imaging signal input from the connector unit 5 to predetermined image processing to output to the display device 7. Moreover, the processor 6 generally controls the entire endoscope system 1. For example, the processor 6 performs control of switching illumination light output by the light source device 8 or switching imaging modes of the endoscope 2.

The display device 7 displays an image corresponding to the imaging signal subjected to image processing by the processor 6. Moreover, the display device 7 displays various kinds of information relating to the endoscope system 1. The display device 7 is constituted of a display panel, such as a liquid crystal display and an organic electroluminescence (EL) display, or the like.

The light source device 8 irradiates illumination light toward a subject (subject to be imaged) from the distal end portion 101 side of the insertion portion 100 of the endoscope 2 via the connector unit 5 and the transmission cable 3. The light source device 8 is constituted of a white light emitting diode (LED) that emits white light, or the like. In the first embodiment, a simultaneous illumination method is applied to the light source device 8, but a frame sequential illumination method is also applicable.

Endoscope System

Next, the endoscope system 1 is described with reference to FIG. 2, which is a block diagram illustrating the endoscope system 1.

Configuration of Endoscope

First, a configuration of the endoscope 2 is described.

Figure 2:
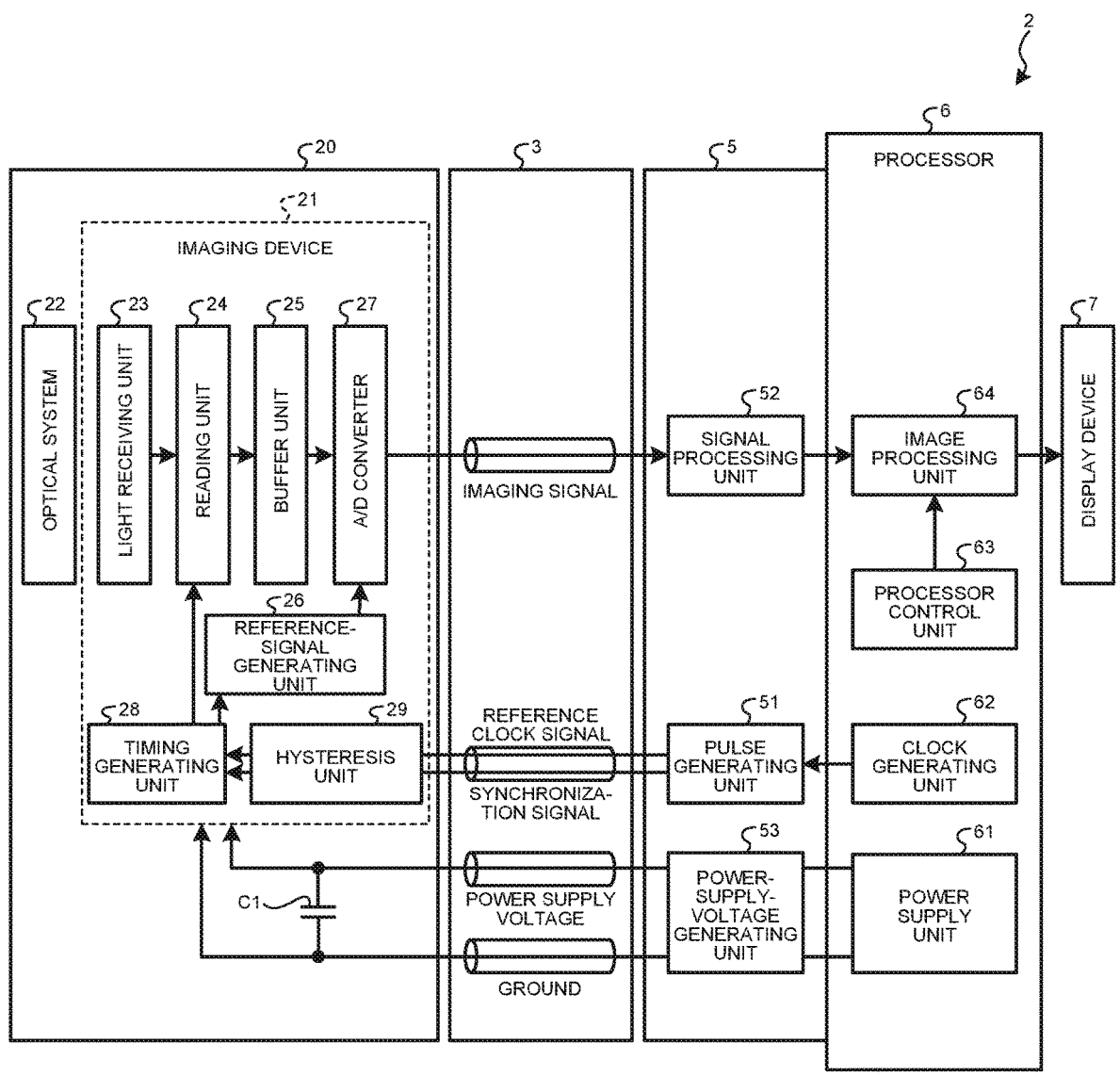
FIG. 2 is a block diagram illustrating the endoscope system according to the first embodiment of the present disclosure.

The endoscope 2 illustrated in FIG. 2 includes the imaging device 20, the transmission cable 3, and the connector unit 5. The imaging device 20 includes an imaging device 21 (imaging chip) and an optical system 22 that forms a subject image on the imaging device 21.

The imaging device 21 includes a light receiving unit 23 having plural pixels that are arranged in a two-dimensional matrix in column and row direction, that receive light from outside, and that generates and outputs an imaging signal according to a reception light amount, a reading unit 24 that sequentially reads an imaging signal that has been subjected to photoelectric conversion by the light receiving unit 23 per column, a buffer unit 25 that impedance-transforms a voltage of the imaging signal sequentially read by the reading unit 24 and amplifies it to one time as large by a voltage follower to output, a reference-signal generating unit 26 that generates and outputs a reference signal having a fluctuation component in phase with the imaging signal generated by the light receiving unit 23 and used for correction processing of the imaging signal, an analog-to-digital (A/D) converter 27 that samples an analog imaging signal output from the buffer unit 25 and a reference signal generated by the reference-signal generating unit 26 at the same timing, and that converts the analog signal into a digital imaging signal to output to the outside, a timing generating unit 28 that generates a timing signal based on a reference clock signal and a synchronization signal, and a hysteresis unit 29 that performs waveform shaping of the reference clock signal and the synchronization signal input from the connector unit 5 through the transmission cable 3, and that outputs the reference clock signal and the synchronization signal subjected to the waveform shaping to the timing generating unit 28. Moreover, the imaging device 21 receives a power supply voltage VDD (for example, 3.3 volts (V)) generated by a power supply unit 61 of the processor 6 described later through the transmission cable 3, together with a ground GND. Between the power supply voltage VDD supplied to the imaging device 21 and the ground GND, a capacitor C1 for stabilizing the power supply is provided. A detailed configuration of the imaging device 21 is described later with reference to FIG. 3.

The optical system 22 is configured using multiple lenses and a prism, and forms a subject image on the light receiving unit 23 of the imaging device 21.

The connector unit 5 includes a pulse generating unit 51 that generates a synchronization signal (including a horizontal synchronizing signal and a vertical synchronizing signal) indicating a start position of each frame based on the reference clock signal (for example, clock signal of 27 megahertz (MHz)) that is supplied by the processor 6 and that is to be a reference of an operation of each component of the endoscope 2, to output to the timing generating unit 28 of the imaging device 20 through the transmission cable 3 together with the reference clock signal, a signal processing unit 52 that is configured using a field programmable gate array (FPGA), application specific integrated circuit (ASIC), or the like, and that subjects the digital imaging signal output from the imaging device 20 through the transmission cable 3 to predetermined image processing, for example, nose reduction processing, to output to the processor 6, and a power-supply-voltage generating unit 53 that is configured using a regulator or the like, and that generates a power supply voltage necessary for driving the imaging device 21 from a power supplied from the processor 6 to output to the imaging device 21.

Configuration of Processor

Next, a configuration of the processor 6 is described.

The processor 6 includes the power supply unit 61 that generates a power supply voltage, and that supplies the generated power supply voltage VDD to the power-supply-voltage generating unit 53 of the connector unit 5 together with the ground GND, a clock generating unit 62 that generates a reference clock signal to be a reference of an operation of each component of the endoscope system 1, and that outputs the reference clock signal to the pulse generating unit 51 of the connector unit 5, a processor control unit 63 that is configured using a central processing unit (CPU) or the like, and that generally controls the entire endoscope system 1, and an image processing unit 64 that converts the digital imaging signal input from the endoscope 2 into an image signal by performing image processing, such as synchronization processing, white balance (WB) adjustment processing, gain adjustment processing, gamma correction processing, digital-to-analog (D/A) conversion processing, and format conversion processing, and that outputs this image signal to the display device 7.

Configuration of Imaging Device

Figure 3:
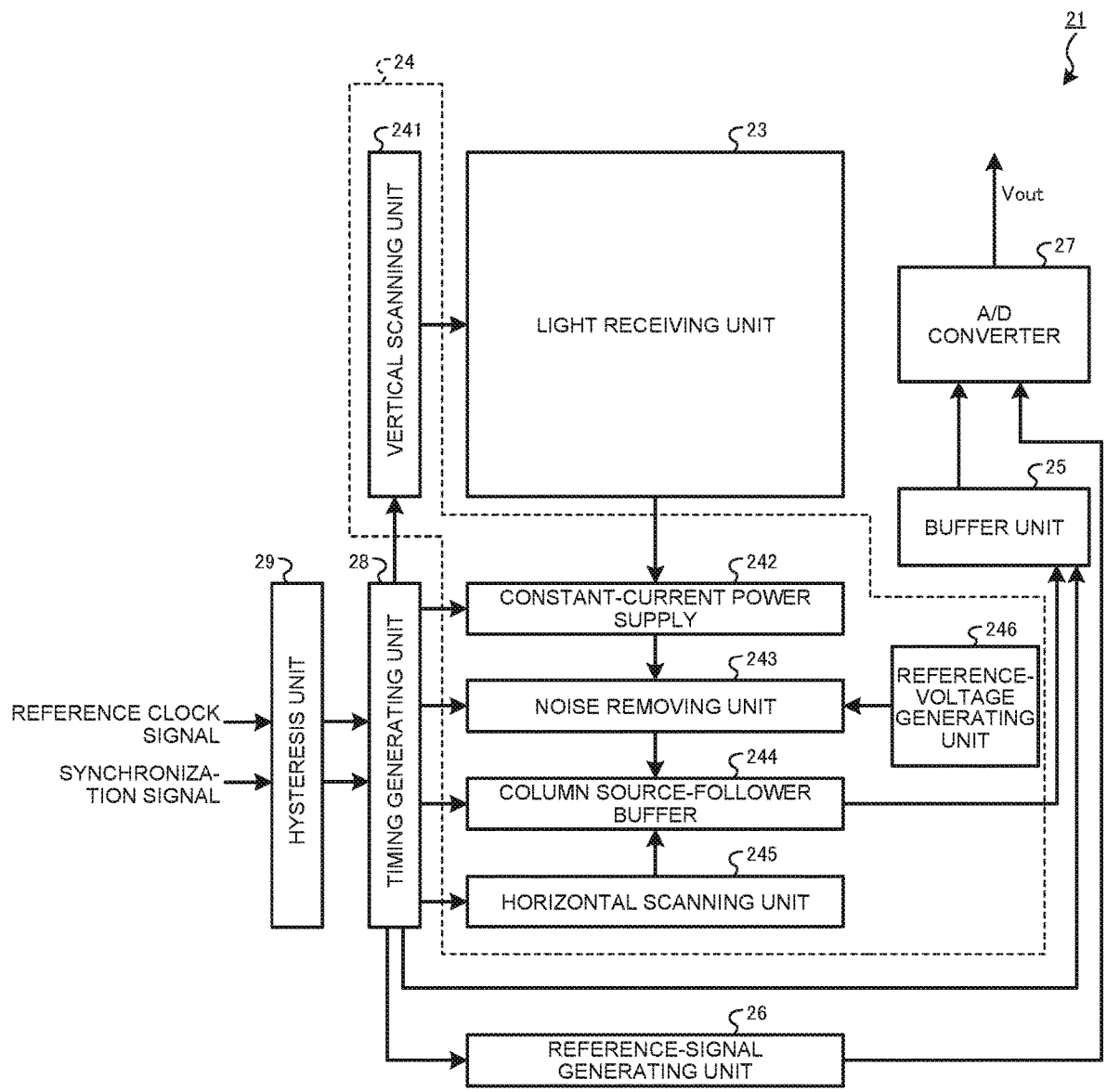
FIG. 3 is a block diagram illustrating a detailed configuration of an imaging device illustrated in FIG. 2.

Next, a detailed configuration of the imaging device 21 described above is described. FIG. 3 is a block diagram illustrating a detailed configuration of the imaging device 21 illustrated in FIG. 2.

As illustrated in FIG. 3, the imaging device 21 includes the light receiving unit 23, the reading unit 24, the buffer unit 25, the reference-signal generating unit 26, the A/D converter 27, the timing generating unit 28, and the hysteresis unit 29.

The light receiving unit 23 has plural pixels that are arranged in a two-dimensional matrix in column and row direction, and that receive light from the outside, and that generate and output an imaging signal according to a reception light amount. A configuration of pixels in the light receiving unit 23 is described in detail in FIG. 4 described later.

The reading unit 24 sequentially reads an imaging signal from the respective pixels of the light receiving unit 23 described later to output to the buffer unit 25. The reading unit 24 includes a vertical scanning unit 241 (row selecting circuit), a constant-current power supply 242, a noise removing unit 243, a column source-follower buffer 244, a horizontal scanning unit 245 (column selecting circuit), and a reference-voltage generating unit 246.

The vertical scanning unit 241 applies driving signals ϕT<M> and ϕR<M> to a selected row (horizontal line)<M> (M=0, 1, 2, . . . , m−1, m) based on the driving signal (ϕT, ϕR, and the like) input from the timing generating unit 28, to drive the respective pixels 230 of the light receiving unit 23 with the constant-current power supply 242, and thereby transfers the imaging signal and a noise signal at the time of pixel reset to a vertical transfer line 239 (first transfer line) described later to output to the noise removing unit 243.

The noise removing unit 243 removes output variations of the respective pixels 230 described later and the noise signal at the time of pixel reset, and outputs the imaging signal generated by photoelectric conversion in the respective pixels 230 described later to the column source-follower buffer 244.

The column source-follower buffer 244 holds the imaging signal from which a noise is removed by the noise removing unit 243 based on the driving signal input from the horizontal scanning unit 245, and amplifies this held imaging signal to output the amplified imaging signal to the buffer unit 25.

The horizontal scanning unit 245 applies a driving signal ϕHCLK<N> to a selected column (vertical line)<N> (N=0, 1, 2, . . . , n−1, n) of the light receiving unit 23 based on a driving signal (ϕHCLK) input from the timing generating unit 28, and transfers the imaging signal generated by photoelectric conversion in the respective pixels 230 to a horizontal transfer line 257 described later through the noise removing unit 243 and the column-source follower buffer 244, to output to the buffer unit 25.

The reference-voltage generating unit 246 generates a clamping voltage VCLP of the noise removing unit 243 from the power supply voltage VDD that is also applied to the light receiving unit 23. Details of a circuit of the reference-voltage generating unit 246 are described later in FIG. 5.

The buffer unit 25 subjects a voltage of the imaging signal sequentially output from the column-source follower buffer 244 to impedance transformation, and amplifies the imaging signal to one time as large by a voltage follower to output to the A/D converter 27. Details of a circuit of the buffer unit 25 are described later in FIG. 4.

The reference-signal generating unit 26 generates a reference signal having a fluctuation component in phase with the imaging signal generated by the light receiving unit 23 and used for correction processing of the imaging signal, to output to the A/D converter 27. Details of a circuit of the reference-signal generating unit 26 are described later in FIG. 6.

The A/D converter 27 samples an analog imaging signal output from the buffer unit 25 and a reference signal generated by the reference-signal generating unit 26 at the same timing, and converts the analog imaging signal into a digital imaging signal (Vout) to output to the outside.

The timing generating unit 28 generates various kinds of driving signals based on a reference clock signal and a synchronization signal input from the hysteresis unit 29, to output to the reading unit 24 described later, the buffer unit 25, the reference-signal generating unit 26, and the A/D converter 27.

The hysteresis unit 29 performs waveform shaping on the reference clock signal and the synchronization signal input through the transmission cable 3, and outputs the reference clock signal and the synchronization signal that have undergone this waveform shaping to the timing generating unit 28.

Configuration of Circuit of Imaging Device

Figure 4:
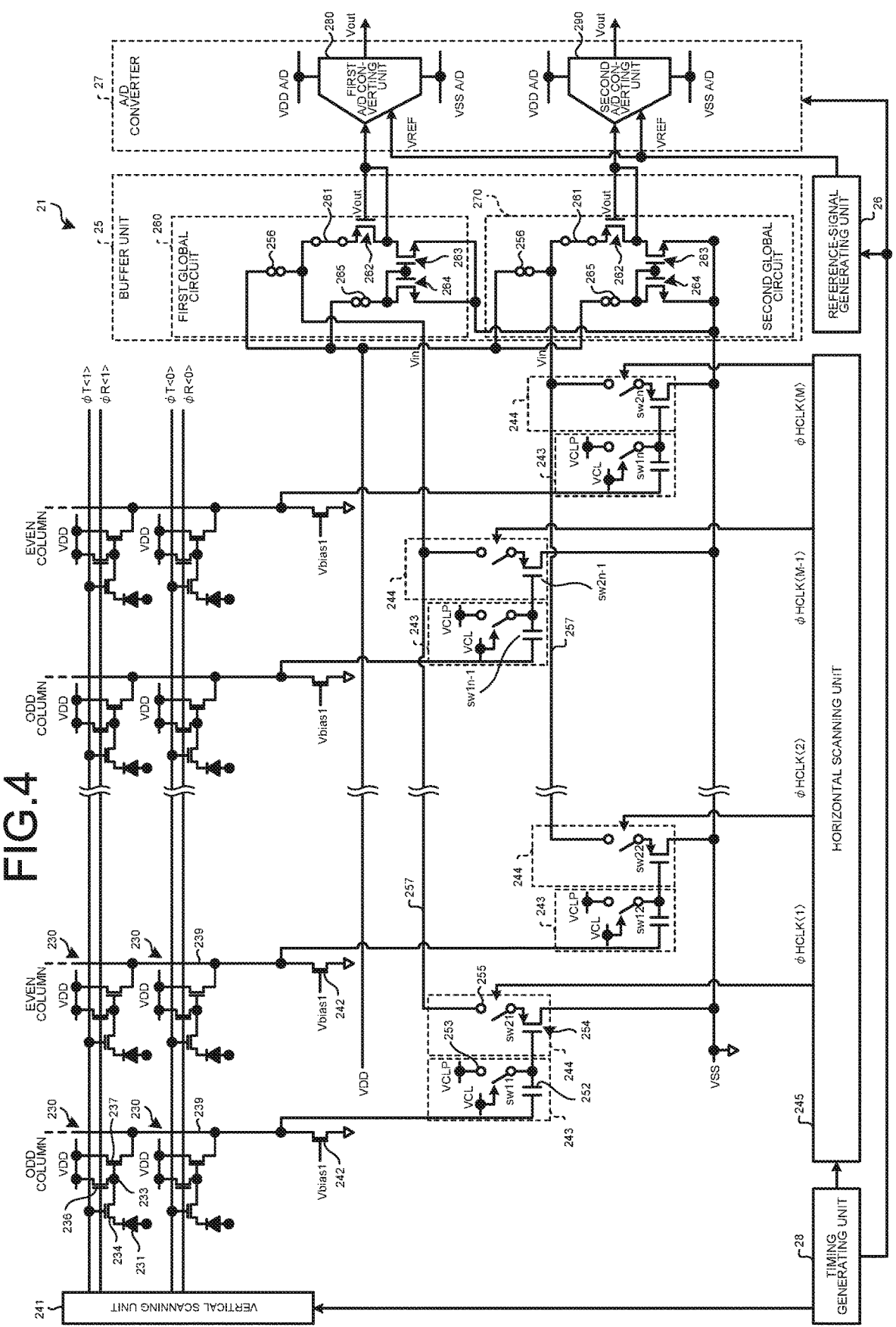
FIG. 4 is a circuit diagram schematically illustrating a configuration of the imaging device according to the first embodiment of the present disclosure.

Next, details of a circuit of the imaging device 21 described above are described. FIG. 4 is a circuit diagram schematically illustrating a configuration of the imaging device 21.

Configuration of Pixel

First a configuration of the pixel 230 is described.

As illustrated in FIG. 4, in the light receiving unit 23 described above, the multiple pixels 230 are arranged in a two-dimensional matrix. Each of the pixels 230 includes a photoelectric converting device 231 (photodiode), a charge converting unit 233, a transfer transistor 234 (first transfer unit), a pixel resetting unit 236 (transistor), and a pixel source-follower transistor 237.

The photoelectric converting device 231 photoelectric converts incident light to signal charge, and accumulates the signal charge. Here, an amount of the signal charge corresponds to an amount of the incident light. A cathode of the photoelectric converting device 231 is connected to one end (e.g., source) of the transfer transistor 234, and an anode is connected to the ground GND in each pixel 230.

The charge converting unit 233 is constituted of a stray diffusion capacitance (FD), and converts an electric charge accumulated by the photoelectric converting device 231 into a voltage.

The transfer transistor 234 transfers the electric charge from the photoelectric converting device 231 to the charge converting unit 233. To a gate of the transfer transistor 234, a signal line to which a driving signal ϕT is supplied is connected, and to the other end (e.g., drain), the charge converting unit 233 is connected. When the driving signal ϕT is supplied from the vertical scanning unit 241 through the signal line, the transfer transistor 234 is turned into an on state, and transfers the electric charge from the photoelectric converting device 231 to the charge converting unit 233.

The pixel resetting unit 236 resets the charge converting unit 233 to be at a predetermined potential. The pixel resetting unit 236 is connected to the power supply voltage VDD at one end, and is connected to the charge converting unit 233 at the other end. To a gate, the signal line to which the driving signal ϕR is supplied is connected. When the driving signal ϕR is supplied from the vertical scanning unit 241 through the signal line, the pixel resetting unit 236 is turned into an on state, and causes the charge converting unit 233 to release the accumulated signal charge, to reset the charge converting unit 233 to be at a predetermined potential.

The pixel source-follower transistor 237 is connected to the power supply voltage VDD (for example, 3.3 V) at one end, and is connected to the vertical transfer line 239 at the other end. To a gate, a signal subjected to voltage conversion (an imaging signal or a signal at the time of reset) by the charge converting unit 233 is input. When the driving signal φT is supplied to the gate of the transfer transistor 234 after a selecting operation described later, an electric charge is read from the photoelectric converting device 231, and is subjected to voltage conversion by the charge converting unit 233, and the pixel source-follower transistor 237 then transfers the electric charge to the vertical transfer line 239.

One end of the constant-current power supply 242 is connected to the vertical transfer line 239, and the other end is connected to the ground GND. To a gate, a bias voltage Vbias1 is applicable. The constant-current power supply 242 drives the pixels 230, and let outputs of the pixels 230 be output to the vertical transfer line 239. The signal output to the vertical transfer line 239 is input to the noise removing unit 243.

Configuration of Noise Removing Unit

Next, a configuration of the noise removing unit 243 is described.

The noise removing unit 243 illustrated in FIG. 4 is arranged for each column of the respective pixels 230. Namely, the noise removing unit 243 is arranged for each of the vertical transfer lines 239. The noise removing unit 243 includes a transfer capacitor 252 (alternating current (AC) coupling capacitor) and a clamp switch 253 (transistor). Note that the noise removing unit 243 functions as a clamp circuit in the first embodiment.

One end of the transfer capacitor 252 is connected to the vertical transfer line 239, and the other end is connected to a column source-follower transistor 254 of the column-source follower buffer 244 described later.

One end of the clamp switch 253 is connected to a signal line to which a clamp voltage VCLP is supplied from the reference-voltage generating unit 246, and the other end is connected to a line connecting the transfer capacitor 252 and the column-source follower buffer 244. To a gate of the clamp switch 253 (transistor), a driving signal φVCL is input from the timing generating unit 28. The imaging signal input to the noise removing unit 243 is an optical noise addition signal including a noise component.

In the noise removing unit 243 thus configured, the clamp switch 253 is turned into an on state when the driving signal φVCL is input to the gate of the clamp switch 253, and the transfer capacitor 252 is reset by the clamping voltage VCLP supplied by the reference-voltage generating unit 246. The imaging signal from which a noise has been removed by the noise removing unit 243 is input to the gate of the column source-follower transistor 254 of the column source-follower buffer 244. Because the noise removing unit 243 does not require a sampling capacitor, the capacitance of the transfer capacitor 252 (AC coupling capacitor) is only necessary to have a capacitance sufficient for input capacitance of the column source-follower buffer 244. Furthermore, having no need for a sampling capacitor, the noise removing unit 243 contributes to reduction of an occupying area in the imaging device 21.

Configuration of Column Source-Follower Buffer

Next, a configuration of the column source-follower buffer 244 is described.

The column source-follower buffer 244 illustrated in FIG. 4 is provided for each column of the respective pixels 230. Namely, the column source-follower buffer 244 is provided for each of the vertical transfer lines 239. The column source-follower buffer 244 includes the column source-follower transistor 254 and a column selecting switch 255. Note that the column source-follower buffer 244 functions as a column circuit in the first embodiment.

One end of the column source-follower transistor 254 is connected to the power supply voltage VSS (hereinafter, "ground GND"), and the other end is connected to one end of the column selecting switch 255. To a gate of the column source-follower transistor 254, the imaging signal from which a noise has been removed by the noise removing unit 243 is input.

One end of the column selecting switch 255 is connected to the other end of the column source-follower transistor 254, and the other end is connected to the horizontal transfer line 257. The column selecting switch 255 is configured using a transistor, and a signal line to supply a driving signal φHCLK<M> from the horizontal scanning unit 245 is connected to a gate of the column selecting switch 255. The column selecting switch 255 is turned into an on state when the driving signal φHCLK<M> is supplied from the horizontal scanning unit 245, and the imaging signal from which a noise is removed by the noise removing unit 243 is transferred to the horizontal transfer line 257. To the horizontal transfer line 257, a horizontal resetting transistor (not illustrated) is connected. When a driving signal is input to the horizontal resetting transistor from the timing generating unit 28, the horizontal resetting transistor is turned into an on state, to reset the horizontal transfer line 257.

In the column source-follower buffer 244 thus configured, when the driving signal φHCLK<M> is applied to the column selecting switch 255 from the timing generating unit 28 through the horizontal scanning unit 245, the column selecting switch 255 is turned into an on state, and the imaging signal from which a noise has been removed by the noise removing unit 243 is sequentially input to the buffer unit 25 through the horizontal transfer line 257.

Configuration of Buffer Unit

Next, a configuration of the buffer unit 25 is described.

The buffer unit 25 illustrated in FIG. 4 forms a voltage follower circuit along with the column source-follower buffers 244 connected thereto, which are sequentially selected by the horizontal scanning unit 245, and subjects a voltage of the input imaging signal to impedance transformation, to output to the A/D converter 27. Specifically, the buffer unit 25 amplifies the input imaging signal to one time as large by the voltage follower, when the column source-follower buffers 244 are sequentially selected by the horizontal scanning unit 245, to output to the A/D converter 27. The buffer unit 25 includes a first global circuit 260 and a second global circuit 270 that are provided respectively for an odd column and an even column of the pixels 230. The first global circuit 260 and the second global circuit 270 function as an impedance transforming unit.

The first global circuit 260 includes a constant-current power supply 256, a switch 261, a first transistor 262, a second transistor 263, a third transistor 264, and a constant-current power supply 265.

One end of the constant-current power supply 256 is connected to the horizontal transfer line 257, and the other end is connected to the power supply voltage VDD. The constant-current power supply 256 reads an imaging signal out to the horizontal transfer line 257. The imaging signal read out to the horizontal transfer line 257 is input to a source of the first transistor 262 through the switch 261 described later. Note that the constant-current power supply 256 functions as a constant-current power supply in the first embodiment.

One end of the switch 261 is connected to the column selecting switch 255 of the column source-follower buffer 244 through the horizontal transfer line 257, and the other end is connected to a source of the first transistor 262. The switch 261 has a resistance similar to the column selecting switch 255 of the column source-follower buffer 244, and is configured using, for example, a transistor. The switch 261 is arranged in the on state all the time, and connects between the horizontal transfer line 257 and the first transistor 262.

One end (source) of the first transistor 262 is connected to the column selecting switch 255 of the column source-follower buffer 244 through the switch 261 and the horizontal transfer line 257, and the other end (drain) is connected to the one end (drain) of the second transistor 263, and a gate is connected to the A/D converter 27. The first transistor 262 is configured using a P-channel metal oxide semiconductor (PMOS).

One end (drain) of the second transistor 263 is connected to the other end (drain) of the first transistor 262 and the gate of the first transistor 262, and the other end is connected to the ground GND, and the gate is connected to the constant-current power supply 265. The second transistor 263 is configured using an N-channel metal oxide semiconductor (NMOS).

One end (drain) of the third transistor 264 is connected to the constant-current power supply 265 (second constant-current power supply), and the other end (source) is connected to the ground GND, and the gate is connected to the constant-current power supply 265.

The first global circuit 260 thus configured forms a voltage follower circuit along with the column source-follower buffers 244 (column side circuit) of an odd column connected thereto, which are sequentially selected by the horizontal scanning unit 245, and subjects a voltage of an imaging signal (Vin) input from the column source-follower buffer 244 to impedance transformation to amplify the imaging signal to one time as large by voltage follower, and output the imaging signal (Vout) to the A/D converter 27.

The second global circuit 270 has the same configuration as the first global circuit 260 described above, and includes the switch 261, the first transistor 262, the second transistor 263, the third transistor 264, and the constant-current power supply 265.

The second global circuit 270 thus configured forms a voltage follower circuit along with the column source-follower buffers 244 (column side circuit) of an even column connected thereto, which are sequentially selected by the horizontal scanning unit 245, and subjects a voltage of the input imaging signal (Vin) to impedance transformation, and outputs the imaging signal (Vout) amplified to one time as large by voltage follower to the A/D converter 27.

The reference-signal generating unit 26 generates a reference signal having a fluctuation component in phase with the imaging signal generated by the pixels 230 and used for correction processing of the imaging signal, to output to the A/D converter 27. Details of a circuit of the reference-signal generating unit 26 are described later with reference to FIG. 6.

The A/D converter 27 is arranged for the odd columns and the even columns of the light receiving unit 23, and includes a first A/D converting unit 280 that converts an analog imaging signal output from the pixel 230 of an odd column into a digital imaging signal, to output to the outside, and a second A/D converting unit 290 that converts an analog imaging signal output from the pixel 230 of an even column into a digital imaging signal, to output to the outside. Details of circuits of the first A/D converting unit 280 and the second A/D converting unit 290 are described in FIG. 7 later.

Configuration of Reference-Voltage Generating Unit

Figure 5:
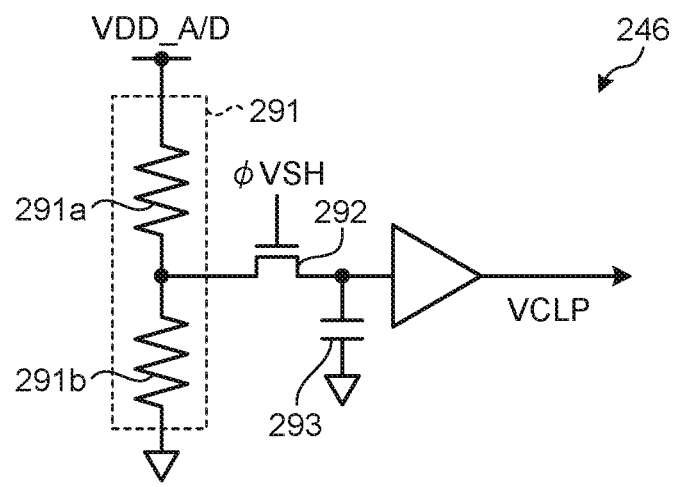
FIG. 5 is a circuit diagram illustrating a configuration of a reference-voltage generating unit according to the first embodiment of the present disclosure.

Next, a configuration of the reference-voltage generating unit 246 illustrated in FIG. 3 is described. FIG. 5 is a circuit diagram illustrating a configuration of the reference-voltage generating unit 246.

The reference-voltage generating unit 246 (constant-voltage-signal generating unit) includes a resistance divider circuit 291 constituted of two resisters 291a and 291b, a switch 292 (transistor) that is driven by a driving signal φVSH applied by the timing generating unit 28, and a sampling capacitor 293 (capacitor) to release from fluctuations by separating from the power supply. One end of the divider circuit 291 is connected to VDD_A/D (for example, 3.3 V), and the other end of the divider circuit 291 is connected to the ground GND.

The reference-voltage generating unit 246 thus configured generates a clamp voltage VCLP of the noise removing unit 243 at timing when the driving signal φVSH drives by driving of the switch 292, to output to the noise removing unit 243.

Configuration of Reference-Signal Generating Unit

Figure 6:
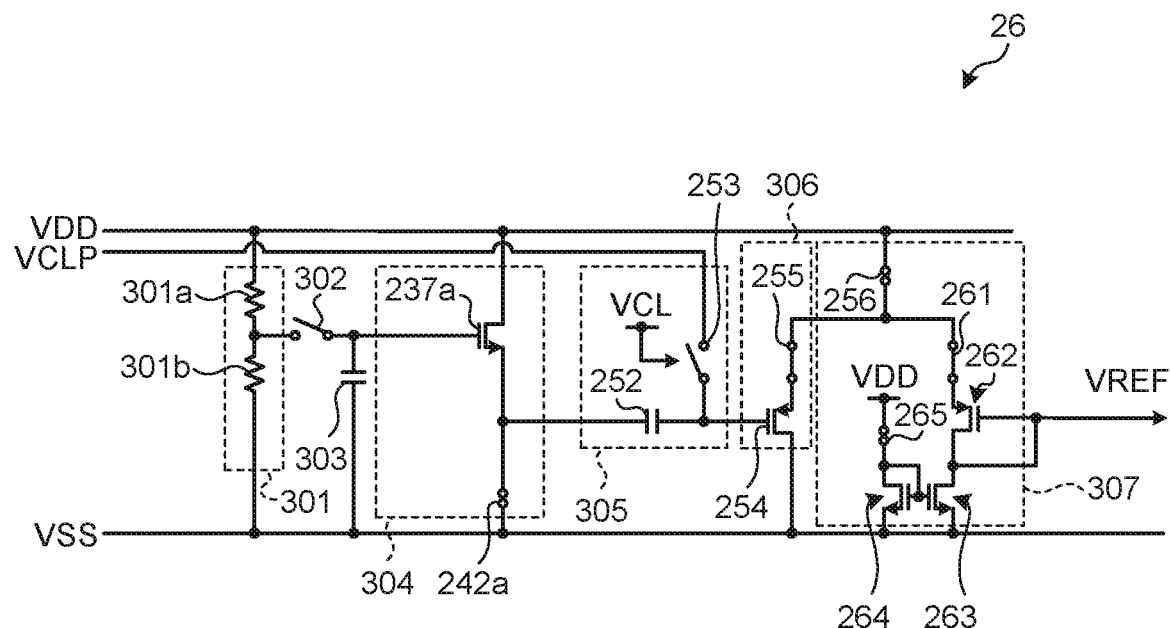
FIG. 6 is a circuit diagram schematically illustrating a configuration of the reference-voltage generating unit according to the first embodiment of the present disclosure.

Next, a detailed configuration of the reference-signal generating unit 26 illustrated in FIG. 3 and FIG. 4 is described. FIG. 6 is a circuit diagram schematically illustrating a configuration of the reference-signal generating unit 26.

The reference-signal generating unit 26 illustrated in FIG. 6 includes a resistance divider circuit 301 constituted of two resistors 301a and 301b, a switch 302 (transistor) that drives by a driving signal applied by the timing generating unit 28, a sampling capacitor 303 to release fluctuations by separating from a power supply, a pixel equivalent circuit 304, a noise-removal equivalent circuit 305, a column equivalent circuit 306, and a buffer equivalent circuit 307.

The pixel equivalent circuit 304 forms a circuit equivalent to each of the pixel source-follower transistor 237 and the constant-current power supply 242 of the pixel 230, and includes a pixel source-follower transistor 237a and a constant-current power supply 242a that drives the pixel source-follower transistor 237a.

One end (drain) of the pixel source-follower transistor 237a is connected to the power supply voltage VDD, and the other end (source) is connected to the constant-current power supply 242a. To a gate, a signal line to which a signal transferred from the sampling capacitor 303 is transferred is connected.

One end of the constant-current power supply 242a is connected to the pixel source-follower transistor 237a, and the other end is connected to the ground GND (VSS). The constant-current power supply 242a drives the pixel source-follower transistor 237a, and lets an output of the pixel source-follower transistor 237a be output to the noise-removal equivalent circuit 305.

The noise-removal equivalent circuit 305 forms a circuit equivalent to the noise removing unit 243 described above, and includes a transfer capacitor 252 (AC coupling capacitor) and a clamp switch 253. Because the noise-removal equivalent circuit 305 is a circuit equivalent to the noise removing unit 243 described above, detailed description thereof is omitted.

The column equivalent circuit 306 forms a circuit equivalent to the column source-follower buffer 244 described above, and includes the column source-follower transistor 254 and the column selecting switch 255. Because the column equivalent circuit 306 is a circuit equivalent to the column source-follower buffer 244 described above, detailed description thereof is omitted.

The buffer equivalent circuit 307 forms a circuit equivalent to the first global circuit 260 described above, and includes the constant-current power supply 256, the switch 261, the first transistor 262, the second transistor 263, the third transistor 264, and the constant-current power supply 265. Because the buffer equivalent circuit 307 is a circuit equivalent to the first global circuit 260 described above, detailed description thereof is omitted.

The reference-signal generating unit 26 thus configured generates a reference signal (VREF) having a fluctuation component in phase with the imaging signal generated by the pixels 230 and used for correction processing of the imaging signal, to output to the A/D converter 27.

Configuration of First A/D Converter

Figure 7:
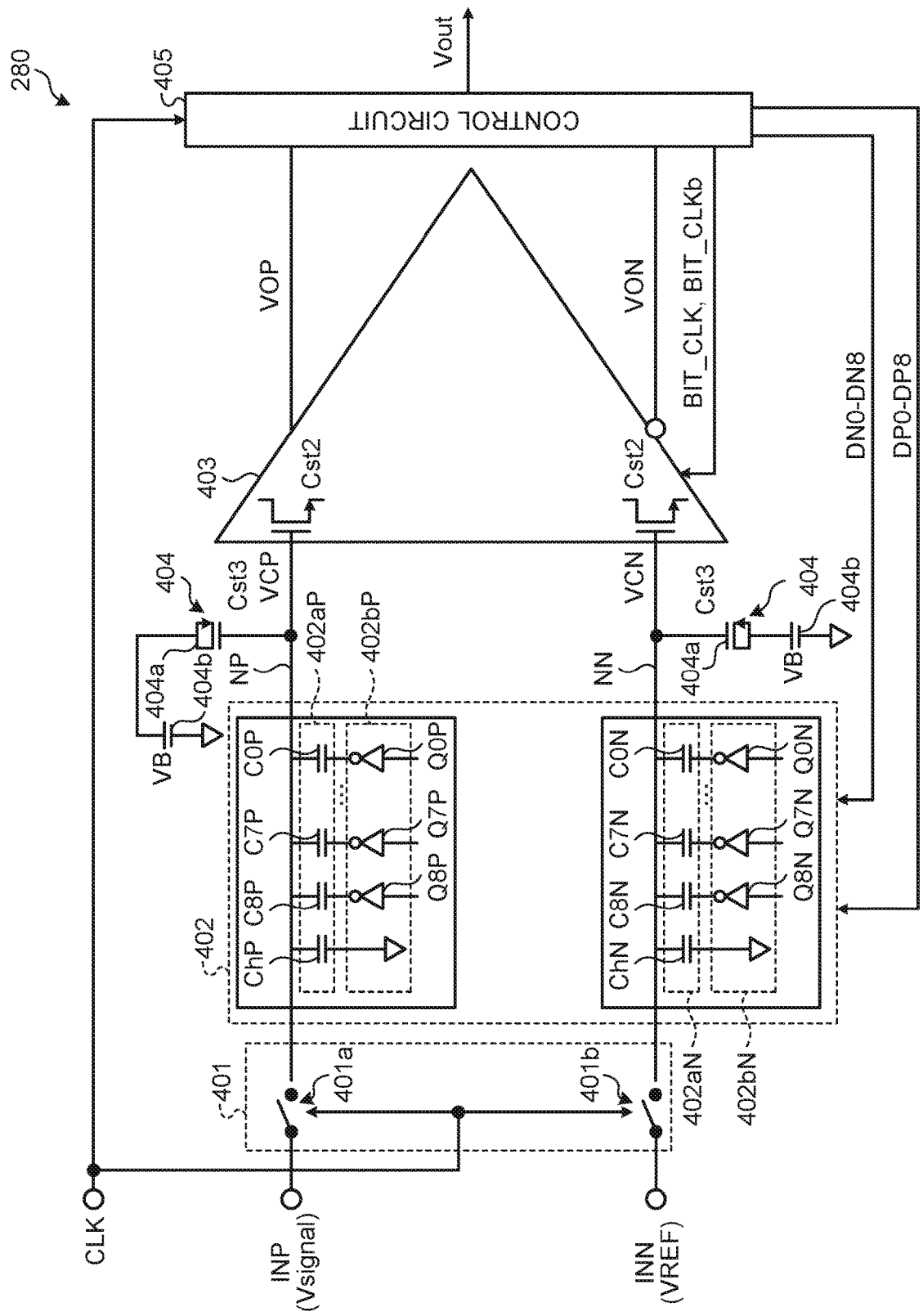
FIG. 7 is a circuit diagram schematically illustrating a configuration of a first analog-to-digital (A/D) converter according to the first embodiment of the present disclosure.

Next, a configuration of the first A/D converting unit 280 is described. FIG. 7 is a circuit diagram schematically illustrating a configuration of the first A/D converting unit 280. Because the first A/D converting unit 280 and the second A/D converting unit 290 has the same circuit configuration, only the configuration of the first A/D converting unit 280 is described in the following, and description of the configuration of the second A/D converting unit 290 is omitted. Moreover, the first A/D converting unit 280 illustrated in FIG. 7 is a successive approximation A/D converter and is an A/D converter of 9-bit output, but not limited thereto, the number of output bit may be changed as appropriate. Note that as long as the first A/D converting unit 280 is an A/D converter capable of reducing power consumption, it is not necessarily required to be a successive approximation A/D converter. For example, a Nyquist A/D converter is applicable.

The first A/D converting unit 280 illustrated in FIG. 7 includes a sampling circuit 401, a capacitive digital-to-analog converter (DAC) circuit 402, a comparator circuit 403, a correction circuit 404, and a control circuit 405.

The sampling circuit 401 samples an analog imaging signal and a reference signal by performing track and hold with respect to a pair of an imaging signal (Vsignal) and a reference signal (VREF) constituting a differential input signal at the same timing based on the clock signal CLK input from the timing generating unit 28. The sampling circuit 401 includes a switch 401a and a switch 401b.

The switch 401a electrically connects the first global circuit 260 and the capacitive DAC circuit 402 when the switch 401a is in an on state, and keeps impedance between the first global circuit 260 and the capacitive DAC circuit 402 to a high impedance state when the switch 401a is in an off state. To the switch 401a, an analog imaging signal is input through a non-inverting input terminal INP. The switch 401a holds and samples the analog imaging signal in a capacitor unit 402aP described later at timing when the switch 401a is switched to the off state from the on state. The switch 401a switches between the on state and the off state based on the clock signal CLK input from the timing generating unit 28.

The switch 401b electrically connects the reference-signal generating unit 26 described above and the capacitive DAC circuit 402 when the switch 401b is in the on state, and keeps impedance between the reference-signal generating unit 26 and the capacitive DAC circuit 402 into a high impedance state when the switch 401b is in an off state. To the switch 401b, the analog reference signal is input through a non-inverting input terminal INN. The switch 401b holds and samples the analog reference signal in a capacitor unit 402aN described later at timing when the switch 401b is switched to the off state from the on state. The switch 401b switches between the on state and the off state based on the clock signal CLK input from the timing generating unit 28.

The capacitive DAC circuit 402 generates an analog signal based on a digital signal (DN0 to DN8, DP0 to DP8) generated by the control circuit 405, and acquires a cumulative residual between a differential input signal and a 9-bit digital signals D0 to D8 by subtracting a reference signal (a reference signal different from the reference signal VREF) from each of the imaging signal and the reference signal sampled and held in the sampling circuit 401. The capacitive DAC circuit 402 outputs a subtraction result that is obtained by subtracting the reference signal from each of the imaging signal and the reference signal to the comparator circuit 403 as the analog imaging signal (INP) and the reference signal (INN) to which the cumulative residual is reflected. The capacitive DAC circuit 402 includes the capacitor unit 402aN, a driving unit 402bN, a capacitor unit 402aP, and a driving unit 402bP.

The capacitor unit 402aP includes an attenuation capacitor ChP and binary capacitors C0P to C8P. The attenuation capacitor ChP is connected between a signal node NP corresponding to a wiring connected to the switch 401a and the ground GND. Moreover, the respective binary capacitors C0P to C8P are connected between the signal node NP and an output unit of the driving unit 402bP. That is, the respective binary capacitors C0P to C8P are arranged such that one electrode is connected to the signal node NP in common connection, and the other electrode is individually connected to an output unit of inverters Q0P to Q8P constituting the driving unit 402bP described later. The binary capacitors C0P to C8P are arranged corresponding to the digital signals DP0 to DP8 that are generated by the control circuit 405. The capacitance values of the respective binary capacitors C0P to C8P differ from each other. For example, the capacitance value of the capacitor C(n+1)P corresponding to the digital signal DP(n+1) is two times as large as the capacitance value of a capacitor CnP corresponding to the digital signal DPn (n is an integer from 0 to 7). That is, the respective capacitance values of the binary capacitors C0P to C8P are weighted by binary number according to a place of respective bits of the digital signals DP0 to DP8.

The capacitor unit 402aN includes attenuation capacitor ChN and binary capacitors C0N to C8N similarly to the capacitor unit 402aP. The attenuation capacitor ChN is connected between a signal node NN, which corresponds to a wiring connected to the switch 401b, and the ground GND. Moreover, the respective binary capacitors C0N to C8N are connected between the signal node NN and an output unit of the driving unit 402bN. That is, the respective binary capacitors C0N to C8N are arranged such that one electrode is connected to the signal node NN in common connection, and the other electrode is individually connected to an output unit of inverters Q0N to Q8N constituting the driving unit 402bN described later. The binary capacitors C0N to C8N are arranged corresponding to the digital signals DN0 to DN8 that are generated by the control circuit 405. The capacitance values of the respective binary capacitors C0N to C8N are also by binary number, similarly to the binary capacitors C0P to C8P. Moreover, the respective capacitance values of the binary capacitors C0N to C8N constituting the capacitor unit 402aN are set to same as the respective capacitance values of the binary capacitors C0P to C8P constituting the capacitor unit 402aP.

The driving unit 402bP includes the inverters Q0P to Q8P. To the inverters Q0P to Q8P, a power supply voltage VDD_A/D is supplied. This means that amplitudes of analog signals output from the respective inverters Q0P to Q8P are equal to the power supply voltage VDD_A/D. The inverters Q0P to Q8P are arranged corresponding to the digital signals DP0 to DP8 that are generated by the control circuit 405. To each of the inverters Q0P to Q8P, each bit of the digital signals DP0 to DP8 is input from the control circuit 405. Moreover, the respective output units of the inverters Q0P to Q8P are connected to the other electrodes of the binary capacitors C0P to C8P.

The inverters Q0P to Q8P generate the reference signal by inverting the digital signals DP0 to DP8 input from the control circuit 405. The binary capacitors C0P to C8P included in the capacitor unit 402aP subtract the reference signal from the imaging signal Vsignal by removing an electric charge based on the reference signal from an electric charge based on the analog imaging signal Vsignal held in the attenuation capacitor ChP by charge redistribution. The capacitor unit 402aP outputs an analog signal VCP, which is the subtraction result, to the comparator circuit 403.

The driving unit 402bN includes the inverters Q0N to Q8N. To the inverters Q0N to Q8N, the power supply voltage VDD_A/D is supplied. This means that amplitudes of reference signals output from the respective inverters Q0N to Q8N are equal to the power supply voltage VDD_A/D. The inverters Q0N to Q8N are arranged corresponding to the digital signals DN0 to DN8 that are generated by the control circuit 405. To each of the inverters Q0P to Q8P, each bit of the digital signals DN0 to DN8 is input from the control circuit 405. Moreover, the respective output units of the inverters Q0N to Q8N are connected to the other electrodes of the binary capacitors C0N to C8N.

The inverters Q0N to Q8N generate the reference signal by inverting the digital signals DN0 to DN8 input from the control circuit 405. The binary capacitors C0N to C8N included in the capacitor unit 402aN subtract the reference signal from the analog reference signal VREF by removing an electric charge based on the reference signal from an electric charge based on the analog reference signal VREF held in the attenuation capacitor ChN by charge redistribution. The capacitor unit 402aN outputs an analog signal VCN, which is the subtraction result, to the comparator circuit 403.

The comparator circuit 403 compares the analog signal VCP based on the analog imaging signal Vsignal and the analog signal VCN based on the analog reference signal VREF, which are input from the capacitive DAC circuit 402, and outputs a digitals signal VIP and a digital signal VON that indicate the comparison result according to the magnitude relationship. Specifically, the comparator circuit 403 outputs a high-level signal as the digital signal VOP when a signal level of the analog imaging signal is higher than a signal level of the analog reference signal, and outputs a low-level signal as the digital signal VON. On the other hand, when a signal level of the analog imaging signal is lower than a signal level of the analog reference signal, the comparator circuit 403 outputs a low level signal as the digital signal VOP, and outputs a high-level signal as the digital signal VON. The comparator circuit 403 is controlled based on an internal clock signal BIT_CLK and an inverse internal clock signal BIT_CLKb that are generated by the control circuit 405 described later.

The correction circuit 404 is arranged in a previous stage of the comparator circuit 403, and outputs a pair of voltage signals in which a stray capacitance in the input transistor is cancelled to the comparator circuit 403. Specifically, the correction circuit 404 cancels a stray capacitance (gate capacitance) of the input transistor of the comparator circuit 403, and thereby corrects a pair of analog signal voltages input to the comparator circuit 403 to output to the comparator circuit 403. The correction circuit 404 includes a correction transistor 404a that cancels a stray capacitance of the input transistor of the comparator circuit 403, and a bias circuit 404b that applies a bias voltage VB to the correction transistor 404a. A gate terminal of the correction transistor 404a is connected to the input terminal of the comparator circuit 403. A drain terminal and a source terminal of the correction transistor 404a are connected to each other, and to the bias circuit 404b. The correction transistor 404a constitutes a metal oxide semiconductor (MOS) capacitor with the gate terminal, and the drain and source terminals connected in common connection. A voltage dependence of a capacitance of the correction transistor 404a has an inverse characteristic to a voltage dependence of the input transistor of the comparator circuit 403. The voltage dependence of the correction transistor 404a is described later.

The control circuit 405 functions as a successive approximation register (SAR) logical circuit, and successively determines respective bit values of the digital signals DP0 to DP8, and the digital signals DN0 to DN8 that correspond to the digital signal VOP and the digital signal VON indicating comparison results by the comparator circuit 403 according to a binary search algorithm. The control circuit 405 supplies the digital signals DP0 to DP8 and the digital signals DN0 to DN8 that correspond to the digital signal VOP and the digital signal VON, respectively, to the capacitive DAC circuit 402. Out of these, the control circuit 405 outputs the digital signals DP0 to DP8 as the digital signals D0 to D8 (Vout) indicating an A/D conversion result. Moreover, the control circuit 405 generates the internal clock signal BIT_CLK and the inverse internal clock signal BIT_CLKb that control the comparator circuit 403, which are then supplied to the comparator circuit 403. The control circuit 405 is controlled based on the clock signal CLK generated by the timing generating unit 28. The control circuit 405 generates the internal clock signal BIT_CLK and the inverse internal clock signal BIT_CLKb in a period in which the clock signal CLK is at high level.

The first A/D converting unit 280 thus configured acquires an A/D conversion result sequentially in 1 bit at a time from the highest level bit (D8) toward the lowest-level bit (D0) among the digital signals D0 to D8. In this A/D conversion process, the comparator circuit 403 compares a signal level (voltage) of the analog imaging signal (INP) in which the cumulative residual up to this time is reflected and a signal level (voltage) of the analog reference signal (INN), each time the subtraction described above is performed by the capacitive DAC circuit 402.

Moreover, a differential input range of the first A/D converting unit 280 is expressed as in Equation (1) below.

$$V_{fs,pp} = 2 \frac{Cdac}{Cdac + Ch + Cst1 + Cst2 + Cst3} \text{VDD}\_A/D \quad (1)$$

Cst1 represents a stray capacitance generated between metal wirings (node wirings), Cst2 represents an input capacitance of the comparator circuit 403, Cst3 represents a MOS capacitance generated by the correction transistor 404a, and Ch represents an attenuation capacitance of the capacitive DAC circuit 402.

In Equation (1) above, when Ch is set so as to obtain Cdac=Ch+Cst1+Cst2+Cst3, a gain factor is 1, and a full scale range is obtained. Therefore, in the first embodiment, the capacitance of the correction transistor 404a is set such that the MOS capacitance value shows a bias voltage dependence inverse to the gate capacitance of the input transistor of the comparator circuit 403.

Characteristic of Correction Transistor

Figure 8:
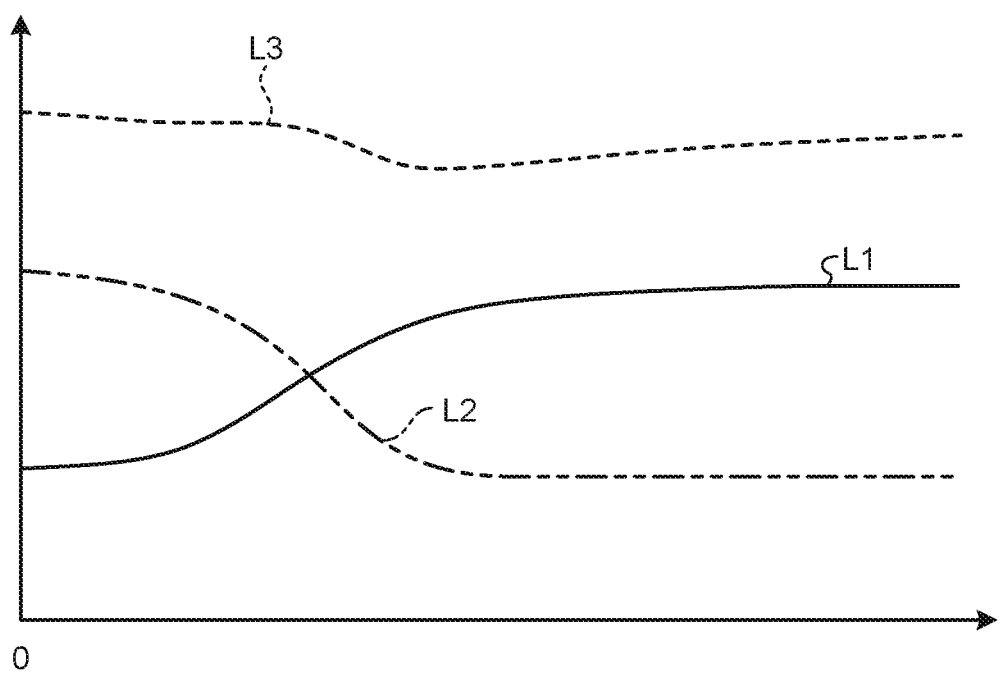
FIG. 8 is a diagram illustrating a relationship of voltage dependent characteristics between an input capacitor of a comparison circuit and an input capacitor of a correction transistor of a correction circuit according to the first embodiment of the present disclosure.

Next, the voltage dependence of the capacitance of the correction transistor 404a and the capacitance of the comparator circuit 403 is described. FIG. 8 is a diagram illustrating a relationship of voltage dependent characteristics between the input capacitance of the comparison circuit 403 and the input capacitance of the correction transistor of the correction circuit 404. In FIG. 8, a horizontal axis represents an input voltage (V) of the comparator circuit 403, and a vertical axis represents a capacitance. Moreover, in FIG. 8, a curve L1 represents a voltage dependence characteristic of the comparator circuit 403, a curve L2 represents a voltage dependence characteristic of the correction transistor 404a, and a curve L3 represents a voltage dependence characteristic of the capacitance (VB parameter) of the correction transistor 404a and the input capacitance of the comparator circuit 403 in a combined capacitance.

As illustrated in FIG. 8, the correction transistor 404a is set such that the capacitance has a bias voltage dependence inverse to the gate capacitance of the input transistor of the comparator circuit 403. Specifically, a user sets the bias voltage VB of the correction transistor 404a appropriately, to make the combined capacitance of the capacitance of the correction transistor 404a and the input capacitance of the comparator circuit 403 substantially flat with respect to changes in an input voltage of the comparator circuit 403. More specifically, as indicated by the curve L2, by setting the bias voltage Vb of the correction transistor 404a appropriately to give a bias voltage dependence inverse to the gate capacitance of the input transistor of the comparator circuit 403, it is possible for a user to make the combined capacitance of the MOS capacitance of the correction transistor 404a and the input capacitance of the comparator circuit 403 substantially flat as indicated by the curve L3.

Figure 9:
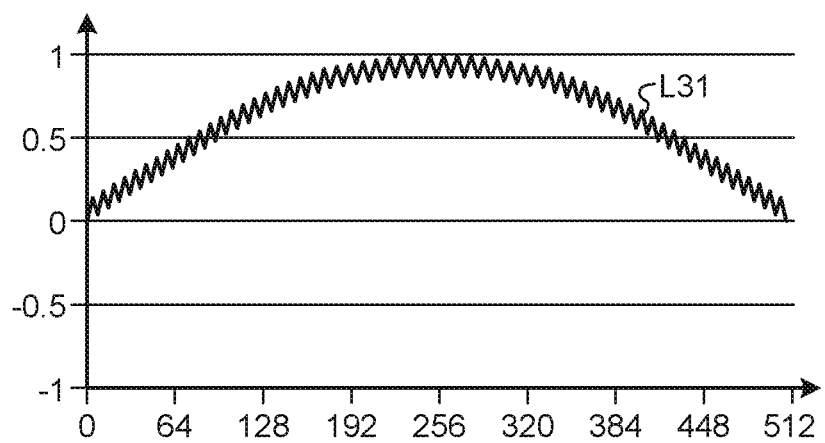
FIG. 9 is a diagram illustrating an integral non-linearity (INL) characteristic of an output signal that is output by a conventional successive approximation A/D converter.
Figure 10:
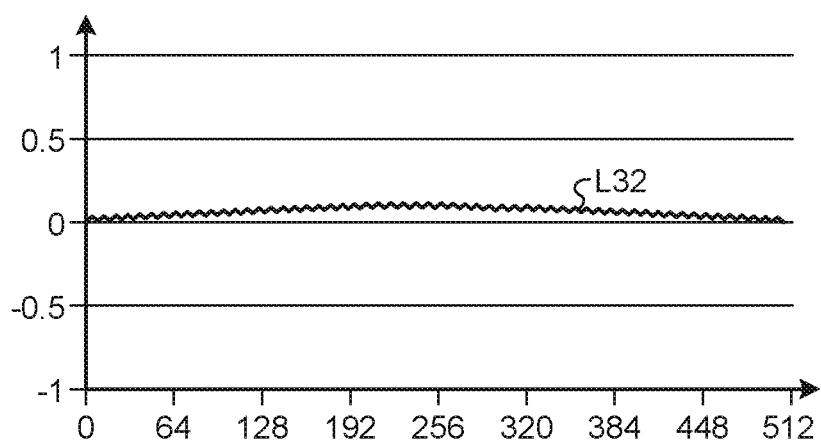
FIG. 10 is a diagram illustrating an INL characteristic of an output signal that is output by the first A/D converter according to the first embodiment of the present disclosure.

FIG. 9 is a diagram illustrating an integral non-linearity (INL) characteristic of an output signal that is output by a conventional successive approximation A/D converter. FIG. 10 shows an INL characteristic of an output signal that is output by the first A/D converting unit 280. In FIG. 9 and FIG. 10, a horizontal axis represents code, and vertical axis represents INL[a.u.]. Moreover, a curve L31 in FIG. 9 represents an INL characteristic of an output signal output by the conventional successive approximation A/D converter, and a curve L32 in FIG. 10 represents an INL characteristic of an output signal output by the first A/D converting unit 280.

As indicated by the curve L32 in FIG. 10, in the first A/D converting unit 280, an output signal is substantially flat, and it enables to prevent fluctuation of gain during A/D conversion. The linearity of the output signal is thereby maintained.

Operation of Imaging Device

Next, an operation of the imaging device 20 is described. FIG. 11A is a timing chart illustrating an operation of the imaging device 20. FIG. 11B is a schematic diagram in which part of the timing chart in a region R1 in FIG. 11A is enlarged. Referring to FIG. 11A, an explanation is made about operations from reading an imaging signal from the pixel 230 of a row <n> of the light receiving unit 23 through outputting a digital imaging signal from the A/D converter 27. Note that, it is assumed that only one photoelectric converting device 231 is included in the pixel 230 for convenience sake in the timing chart illustrated in FIG. 11A. When plural photoelectric converting devices 231 are included in the pixel 230 (in the case of shared pixel), an operation corresponding to one image signal line in this timing chart is repeated as many times as the number of the photoelectric converting devices 231 included in the pixel 230. FIG. 11A illustrates, sequentially from the top most line, the driving signal ϕR, the driving signal ϕT, the driving signal ϕVCL, the driving signals SW21 to SW2n, voltages VIN1 to VINn of the transfer capacitor 252, the output voltage Vout of the buffer unit 25, conversion timing of the A/D converter 27, the reference clock CLK, output timing of a conversion result of the A/D converter 27, and the reference signal VREF. Furthermore, FIG. 11B illustrates, sequentially from the top most line, the reference signal VREF, the output voltage Vout of the buffer unit 25, an operation mode of the A/D converter 27, and a difference obtained by subtracting the reference signal VREF from the output voltage Vout of the buffer unit 25 (Vout−VREF).

As illustrated in FIG. 11A and FIG. 11B, first, the timing generating unit 28 turns on the clamp switch 253 (the driving signal ϕVCL is high), turns on the pixel resetting unit 236 (the pulsed driving signal ϕR<0> is high), and turns off the transfer transistor 234 (the pulsed driving signal ϕT<0> is low) (time T1). With this, a noise signal including variations specific to the pixel 230 to be read, a noise at the time of pixel reset, and the like is output to the vertical transfer line 239 from the pixel 230. At this time, by maintaining the on state of the clamp switch 253 (the driving signal ϕVCL is high), the gate of the column source-follower transistor 254 of the column source-follower buffer 244 is to be a voltage of the clamp voltage VCLP, and the transfer capacitor 252 is charged with VRST−VCLP.

Next, the timing generating unit 28 turns on the transfer transistor 234 (the pulsed driving signal ϕT<0> is high) while the clamp switch 253 is off (the driving signal ϕVCL is low). With this, the charge converting unit 233 reads out a signal photoelectric-converted by the photoelectric converting device 231 to the vertical transfer line 239 (time T2). In this state, an imaging signal VSIG subjected to voltage conversion by the charge converting unit 233 is transferred to the vertical transfer line 239. By this operation, the transfer capacitor 252 is charged with VCLP−(VRST1−VSIG1). Thus, the imaging signal (optical signal) from which a noise signal is removed is output to the gate of the column source-follower transistor 254 of the column source-follower buffer 244 through the transfer capacitor 252. The signal output to the gate of the column source-follower transistor 254 of the column source-follower buffer 244 is a signal sampled based on the clamp voltage VCLP.

Subsequently, the timing generating unit 28 turns on the column selecting switch 255 (the driving signal SW21 is high) (time T3), and the imaging signal Vout (VCLP−(VRST1−VSIG1) charged in the transfer capacitor 252 is thereby output to the A/D converter 27 through the column source-follower buffer 244 and the first global circuit 260.

Thereafter, the timing generating unit 28 switches the column selecting switch 255 between on and off (the driving signal SW21 is low, the driving signal SW22 is high) (time T4), and the imaging signal Vout (VCLP−(VRST2−VSIG2) charged in the transfer capacitor 252 is thereby output to the A/D converter 27 through the column source-follower buffer 244 and the first global circuit 260. At this time, the A/D converter 27 subjects the imaging signal Vout output from the transfer capacitor 252 to A/D conversion based on the reference signal VREF output from the reference-signal generating unit 26, and outputs the digital imaging signal D1 to the outside.

Subsequently, the timing generating unit 28 switches the column selecting switch 255 between on and off sequentially (the driving signals SW22 to SW2n) (time TN), the imaging signal Vout (VCLP−(VRSTn−VSIGn)) charged in the transfer capacitor 252 is thereby output to the A/D converter 27 sequentially through the column source-follower buffer 244 and the first global circuit 260. At this time, the A/D converter 27 subjects the imaging signal Vout sequentially output from the transfer capacitor 252 to A/D conversion based on the reference signal VREF output from the reference-signal generating unit 26, and sequentially outputs the digital imaging signal D2 to DN to the outside.

By repeating the operation as described above as many time as the number of columns of the light receiving unit 23 (or as many times as the number of columns to be read), a digital imaging signal in which a fluctuation component in phase with the imaging signal is cancelled is output to the outside. Furthermore, by repeating the reading operation for one line as many times as the number of pixel rows (or as many times as the number of rows to be read), the imaging device 20 outputs a digital imaging signal corresponding to one frame to the outside.

Moreover, as illustrated in FIG. 11B, while the reference signal VREF and the imaging signal Vout have a common mode noise, the difference (Vout-VREF) between the output voltage Vout of the buffer unit 25 and the reference signal VREF is not influenced by the common mode noise. The A/D converter 27 samples the output voltage Vout input from the buffer unit 25 and the reference signal VREF generated by the reference-signal generating unit 26 at the same timing, and outputs the digital imaging signal Vout to the outside. As a result, the A/D conversion result is not influenced by the common mode noise.

According to the first embodiment of the present disclosure described above, the first global circuit 260 serves as a voltage follower circuit when the column source-follower buffer 244 (column side circuit) of an odd column that is sequentially selected by the horizontal scanning unit 245 is connected to the first global circuit 60, performs impedance transformation with respect to a voltage of the imaging signal (Vin) input from the column source-follower buffer 244, amplifies the imaging signal to an amplification factor of one time as large by voltage follower, and outputs the imaging signal (Vout). Therefore, it is possible to make the maximum use of a level of the imaging signal output by the column source-follower buffer 244.

Moreover, according to the first embodiment of the present disclosure, when outputting to the A/D converter 27 that operates at a power supply voltage lower than that of the pixel 230, the input dynamic range and the linearity of the A/D converter 27 can be maintained.

Furthermore, according to the first embodiment, an input referred noise of the column source-follower buffer 244 can be reduced.

Moreover, according to the first embodiment of the present disclosure, because the reference-signal generating unit 26 generates a reference signal having a fluctuation component in phase with an imaging signal that is generated by the pixel 230, it is possible to convert the imaging signal into a digital imaging signal to be output, in a condition practically not influenced by a common mode noise.

Furthermore, according to the first embodiment of the present disclosure, because a capacitor connected to the input terminal of the comparator circuit 403 can be made substantially flat with respect to changes in an input voltage of the comparator circuit 403, it is possible to prevent degradation of the linearity of an output signal that is output by the A/D converter 27.

First Modification of First Embodiment

Next, a first modification of the first embodiment of the present disclosure is described. The first modification of the first embodiment differs in a configuration of the reference-signal generating unit 26 according to the first embodiment described above. In the following, a configuration of the reference-signal generating unit 26 according to the first modification of the first embodiment is described. Note that like reference symbols are assigned to like components as the endoscope system 1 according to the first embodiment described above, and description thereof is omitted.

Configuration of Reference-Signal Generating Unit

Figure 12:
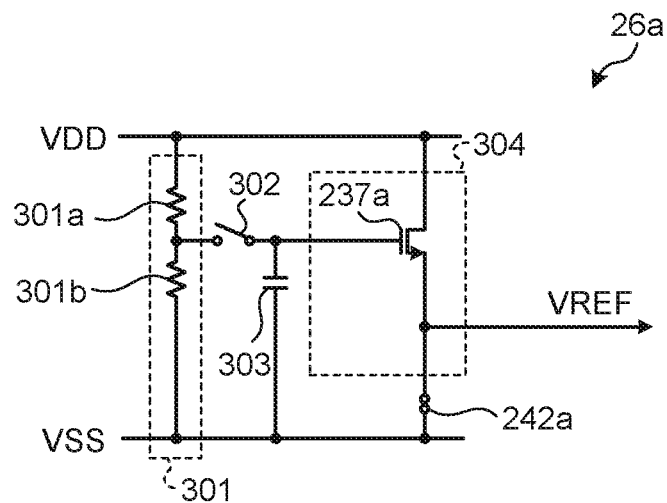
FIG. 12 is a circuit diagram schematically illustrating a configuration of a reference-signal generating unit according to a first modification of the first embodiment of the present disclosure.

FIG. 12 is a circuit diagram schematically illustrating a configuration of the reference-signal generating unit according to a first modification of the first embodiment of the present disclosure.

A reference-signal generating unit 26a illustrated in FIG. 12 has a configuration in which the noise-removal equivalent circuit 305, the column equivalent circuit 306, and the buffer equivalent circuit 307 are omitted from the reference-signal generating unit 26 according to the first embodiment described above, and includes the resistance divider circuit 301 constituted of two resistors 301a and 301b, the switch 302 (transistor) that drives by a driving signal applied by the timing generating unit 28, the sampling capacitor 303 to release fluctuations by separating from a power supply, and the pixel equivalent circuit 304.

According to the first modification of the first embodiment of the present disclosure described above, it is possible to generate a reference signal that has a fluctuation component in phase with an imaging signal generated by the pixel 230, and that is used for correction processing of the imaging signal to be output to the A/D converter 27, and is possible to reduce a chip area in the imaging device 21.

Second Modification of First Embodiment

Next, a second modification of the first embodiment of the present disclosure is described. The second modification of the first embodiment differs in a configuration of the reference-signal generating unit 26 according to the first embodiment. In the following, a configuration of a reference-signal generating unit according to the second modification of the first embodiment is described. Note that like reference symbols are assigned to like components as the endoscope system 1 according to the first embodiment described above, and description thereof is omitted.

Configuration of Reference-Signal Generating Unit

Figure 13:
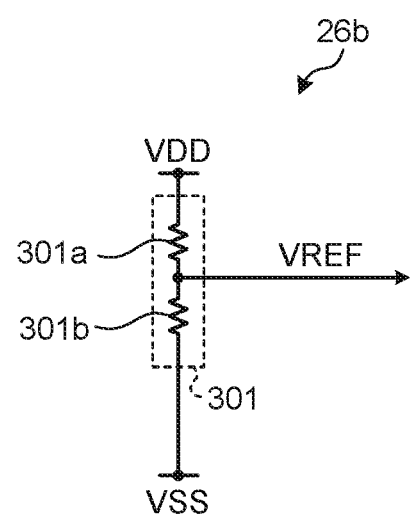
FIG. 13 is a circuit diagram schematically illustrating a configuration of a reference-signal generating unit according to a second modification of the first embodiment of the present disclosure.

FIG. 13 is a circuit diagram schematically illustrating a configuration of the reference-signal generating unit according to the second modification of the first embodiment of the present disclosure.

A reference-signal generating unit 26b illustrated in FIG. 13 has a configuration in which the switch 302 (transistor), the sampling capacitor 303 (capacitor), the pixel equivalent circuit 304, the noise-removal equivalent circuit 305, the column equivalent circuit 306, and the buffer equivalent circuit 307 are omitted from the reference-signal generating unit 26 according to the first embodiment described above, and includes the resistance divider circuit 301 constituted of two resistors 301a and 301b.

According to the second modification of the first embodiment of the present disclosure described above, it is possible to generate a reference signal that has a fluctuation component in phase with an imaging signal generated by the pixel 230, and that is used for correction processing of the imaging signal to be output to the A/D converter 27, and is possible to reduce a chip area in the imaging device 21.

Second Embodiment

Next, a second embodiment of the present disclosure is described. The second embodiment differs in a configuration of the imaging device 21 according to the first embodiment described above. In the following, after describing a configuration of an imaging device according to the second embodiment, an operation of the imaging device according to the second embodiment is described. Note that like reference symbols are assigned to like components as the endoscope system 1 according to the first embodiment described above, and description thereof is omitted.

Configuration of Circuit of Imaging Device

Figure 14:
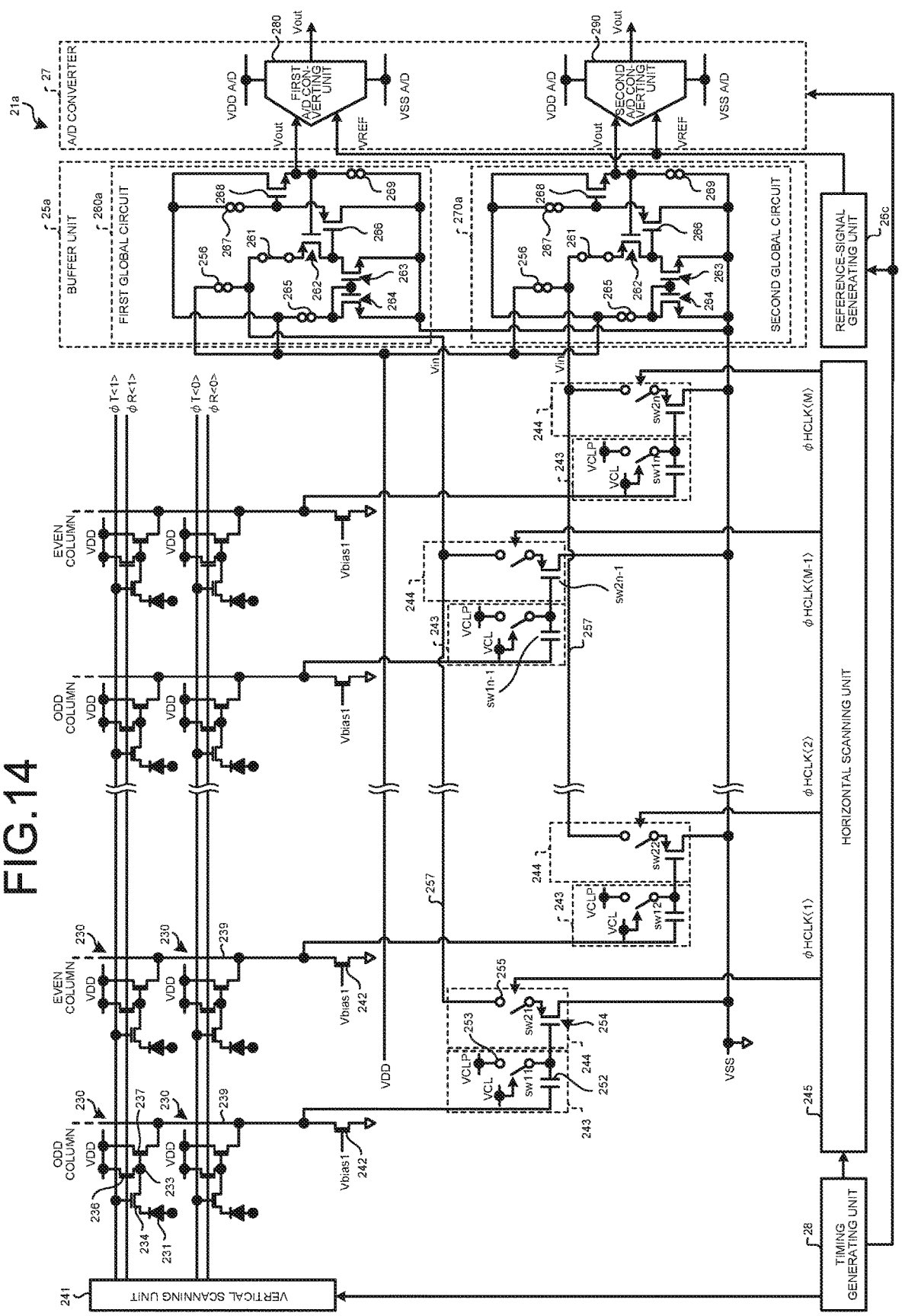
FIG. 14 is a circuit diagram schematically illustrating a configuration of an imaging device according to a second embodiment of the present disclosure.

FIG. 14 is a circuit diagram schematically illustrating a configuration of the imaging device according to the second embodiment of the present disclosure. An imaging device 21a illustrated in FIG. 14 includes a buffer unit 25a and a reference-signal generating unit 26c, in place of the buffer unit 25 and the reference-signal generating unit 26 of the imaging device 21 according to the first embodiment described above.

Configuration of Buffer Unit

First, a configuration of the buffer unit 25a is described. The buffer unit 25a forms a voltage follower circuit along with the column source-follower buffers 244 connected thereto, which are sequentially selected by the horizontal scanning unit 245, amplifies an input imaging signal to one time as large by the voltage follower, to output to the A/D converter 27. The buffer unit 25a includes a first global circuit 260a and a second global circuit 270a that are provided respectively for an odd column and an even column of the pixels 230. The first global circuit 260a and the second global circuit 270a function as an impedance transforming unit.

The first global circuit 260a includes a fourth transistor 266, a constant-current power supply 267, a fourth transistor 266, a constant-current power supply 267, a fifth transistor 268, and a constant-current power supply 269, in addition to the configuration of the first global circuit 260 according to the first embodiment described above.

One end (source) of the fourth transistor 266 is connected to the constant-current power supply 267, and the other end (drain) is connected to the ground GND, and a gate is connected to the column selecting switch 255 of the column source-follower buffer 244 through the first transistor 262 and the horizontal transfer line 257. The fourth transistor 266 is configured using a PMOS.

One end of the constant-current power supply 267 is connected to the power supply voltage VDD, and the other end is connected to one end (source) of the fourth transistor 266 and a gate of the fifth transistor 268. In the second embodiment, the constant-current power supply 267 functions as a constant-current power supply.

One end (drain) of the fifth transistor 268 is connected to the power supply voltage VDD, the other end (source) is connected to the constant-current power supply 269, and a gate is connected to the constant-current power supply 267. The fifth transistor 268 is configured using NMOS.

One end of the constant-current power supply 269 is connected to the ground GND, and the other end is connected to the other end (source) of the fifth transistor 268. In the second embodiment, the constant-current power supply 269 functions as a constant-current power supply.

The first global circuit 260a thus configured has a source follower structure in an output stage. Therefore, when the column source-follower buffer 244 (column side circuit) sequentially selected by the horizontal scanning unit 245 is connected, the first global circuit 260a forms a voltage follower circuit, and outputs an imaging signal (Vout) obtained by amplifying an input imaging signal (Vin) to one time as large by the voltage follower to the A/D converter 27.

The second global circuit 270a has the same configuration as the first global circuit 260a described above, and includes the constant-current power supply 256, the switch 261, the first transistor 262, the second transistor 263, the third transistor 264, and the constant-current power supply 265, the fourth transistor 266, the constant-current power supply 267, the fifth transistor 268, and the constant-current power supply 269.

The second global circuit 270a thus configured forms a voltage follower circuit along with the column source-follower buffers 244 (column side circuit) of an even column connected thereto, which are sequentially selected by the horizontal scanning unit 245, and outputs an imaging signal (Vout) obtained by amplifying an input imaging signal (Vin) to one time as large by voltage follower, to the A/D converter 27.

The reference-signal generating unit 26c generates a reference signal having a fluctuation component in phase with an imaging signal generated by the pixel 230 and used for correction processing of the imaging signal, to output to the A/D converter 27. Details of a circuit of the reference-signal generating unit 26c are described in FIG. 15 later.

Configuration of Reference-Signal Generating Unit

Figure 15:
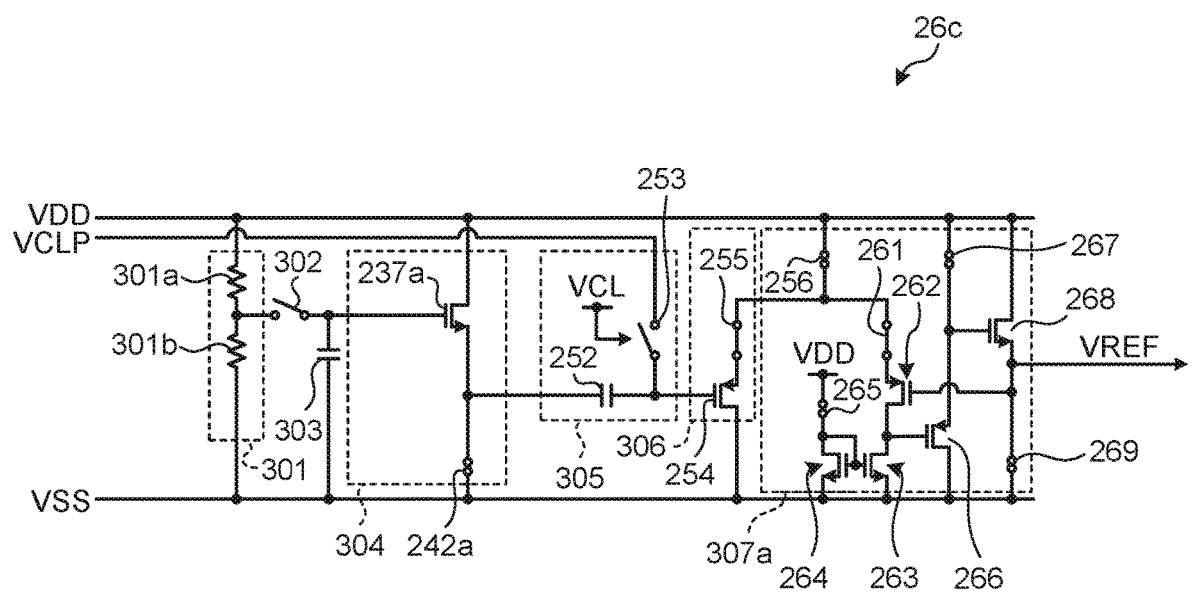
FIG. 15 is a circuit diagram schematically illustrating a configuration of a reference-signal generating unit according to the second embodiment of the present disclosure.

Next, a detailed configuration of the reference-signal generating unit 26c described in FIG. 14 is described. FIG. 15 is a circuit diagram schematically illustrating a configuration of a reference-signal generating unit 26c.

The reference-signal generating unit 26c illustrate in FIG. 15 includes a buffer equivalent circuit 307a in place of the buffer equivalent circuit 307 of the reference-signal generating unit 26 according to the first embodiment described above.

The buffer equivalent circuit 307a forms a circuit equivalent to the first global circuit 260a, and includes the constant-current power supply 256, the switch 261, the first transistor 262, the second transistor 263, the third transistor 264, and the constant-current power supply 265, the fourth transistor 266, the constant-current power supply 267, the fifth transistor 268, and the constant-current power supply 269. Because the buffer equivalent circuit 307a is a circuit equivalent to the first global circuit 260a described above, detailed description thereof is omitted.

The reference-signal generating unit 26c thus configured generates a reference signal (VREF) having a fluctuation component in phase with the imaging signal generated by the pixel 230 and used for correction processing of the imaging signal, to output to the A/D converter 27.

Operation of Imaging Device

Figure 16A:
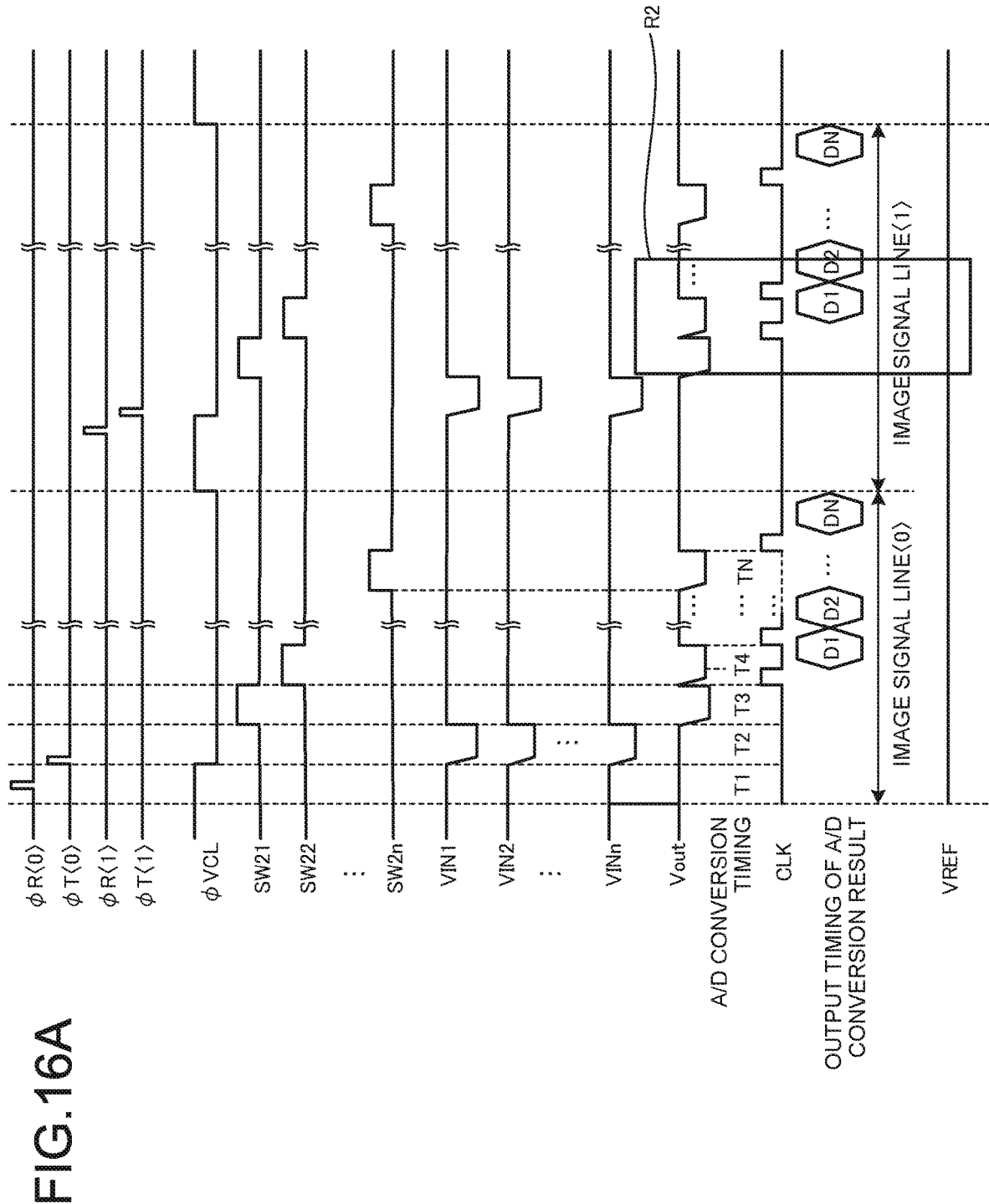
FIG. 16A is a timing chart illustrating an operation of the imaging device according to the second embodiment of the present disclosure.

Next, an operation of the imaging device 20 is described. FIG. 16A is a timing chart illustrating an operation of the imaging device 20. FIG. 16B is a schematic diagram in which part of the timing chart in a region R2 in FIG. 16A is enlarged. Referring to FIG. 16A, an explanation is made about operations from reading an imaging signal from the pixel 230 of a row <n> of the light receiving unit 23 through outputting a digital imaging signal from the A/D converter 27. Note that, it is assumed that only one photoelectric converting device 231 is included in the pixel 230 for convenience sake in the timing chart illustrated in FIG. 16A. When plural photoelectric converting device 231s are included in the pixel 230 (in the case of shared pixel), an operation corresponding to one image signal line in this timing chart is repeated as many times as the number of the photoelectric converting devices 231 included in the pixel 230. FIG. 16A illustrates, sequentially from the top most line, the driving signal φR, the driving signal φT, the driving signal φVCL, the driving signals SW21 to SW2n, voltages VIN1 to VINn of the transfer capacitor 252, the output voltage Vout of the buffer unit 25a, conversion timing of the A/D converter 27, the reference clock CLK, output timing of a conversion result of the A/D converter 27, and the reference signal VREF. Furthermore, FIG. 16B illustrates, sequentially from the top most line, the reference signal VREF, the output voltage Vout of the buffer unit 25, the reference clock CLK, an operation mode of the A/D converter 27, and a difference obtained by subtracting the reference signal VREF from the output voltage Vout of the buffer unit 25a (Vout−VREF).

As illustrated in FIG. 16A and FIG. 16B, first, the timing generating unit 28 turns on the clamp switch 253 (the driving signal φVCL is high), turns on the pixel resetting unit 236 (the pulsed driving signal φR<0> is high), and turns off the transfer transistor 234 (the pulsed driving signal φT<0> is low) (time T1). With this, a noise signal including variations specific to the pixel 230 to be read, a noise at the time of pixel reset, and the like is output to the vertical transfer line 239 from the pixel 230. At this time, by maintaining the on state of the clamp switch 253 (the driving signal φVCL is high), the gate of the column source-follower transistor 254 of the column source-follower buffer 244 is to be a voltage of the clamp voltage VCLP, and the transfer capacitor 252 is charged with VRST-VCLP.

Next, the timing generating unit 28 turns on the transfer transistor 234 (the pulsed driving signal φT<0> is high) while the clamp switch 253 is off (the driving signal φVCL is low). With this, the charge converting unit 233 reads out a charge-converted signal subjected to photoelectric conversion by the photoelectric converting device 231 to the vertical transfer line 239 (time T2). In this state, an imaging signal VSIG subjected to voltage conversion by the charge converting unit 233 is transferred to the vertical transfer line 239. By this operation, the transfer capacitor 252 is charged with VCLP−(VRST1−VSIG1). Thus, the imaging signal (optical signal) from which a noise signal is removed is output to the gate of the column source-follower transistor 254 of the column source-follower buffer 244 through the transfer capacitor 252. The signal output to the gate of the column source-follower transistor 254 of the column source-follower buffer 244 is a signal sampled based on the clamp voltage VCLP.

Subsequently, the timing generating unit 28 turns on the column selecting switch 255 (the driving signal SW21 is high) (time T3), and the imaging signal Vout (VCLP−(VRST1−VSIG1) charged in the transfer capacitor 252 is thereby output to the A/D converter 27 through the column source-follower buffer 244 and the first global circuit 260a.

Thereafter, the timing generating unit 28 switches the column selecting switch 255 between on and off (the driving signal SW21 is low, the driving signal SW22 is high) (time T4), and the imaging signal Vout (VCLP−(VRST2−VSIG2) charged in the transfer capacitor 252 is thereby output to the A/D converter 27 through the column source-follower buffer 244 and the first global circuit 260a. At this time, the A/D converter 27 subjects the imaging signal Vout output from the transfer capacitor 252 to A/D conversion based on the reference signal VREF output from the reference-signal generating unit 26, and outputs the digital imaging signal D1 to the outside.

Subsequently, the timing generating unit 28 switches the column selecting switch 255 between on and off sequentially (the driving signals SW22 to SW2n) (time TN), the imaging signal Vout (VCLP−(VRSTn−VSIGn) charged in the transfer capacitor 252 is thereby output to the A/D converter 27 sequentially through the column source-follower buffer 244 and the first global circuit 260a. At this time, the A/D converter 27 subjects the imaging signal Vout sequentially output from the transfer capacitor 252 to A/D conversion based on the reference signal VREF output from the reference-signal generating unit 26c, and sequentially outputs the digital imaging signals D2 to DN to the outside.

By repeating the operation as described above as many time as the number of columns of the light receiving unit 23 (or as many times as the number of columns to be read), a digital imaging signal in which a fluctuation component in phase with the imaging signal is cancelled is output to the outside. Furthermore, by repeating the reading operation for one line as many times as the number of pixel rows (or as many times as the number of rows to be read), the imaging device 20 outputs a digital imaging signal corresponding to one frame to the outside.

Moreover, as illustrated in FIG. 16B, while the reference signal VREF and the imaging signal Vout have a common mode noise, the difference (Vout−VREF) between the output voltage Vout of the buffer unit 25 and the reference signal VREF is not influenced by the common mode noise. The A/D converter 27 samples the output voltage Vout input from the buffer unit 25 and the reference signal VREF generated by the reference-signal generating unit 26c at the same timing, and outputs the digital imaging signal Vout to the outside. As a result, the A/D conversion resultant is not influenced by the common mode noise.

According to the second embodiment of the present disclosure described above, the first global circuit 260a serves as a voltage follower circuit when the column source-follower buffer 244 (column side circuit) of an odd column that is sequentially selected by the horizontal scanning unit 245 is connected to the first global circuit 260a, performs impedance transformation with respect to a voltage of the imaging signal (Vin) input from the column source-follower buffer 244, amplifies the imaging signal to an amplification factor to one time by voltage follower, and outputs the imaging signal (Vout). Therefore, it is possible to make the maximum use of a level of the imaging signal output by the column source-follower buffer 244.

Moreover, according to the second embodiment of the present disclosure, by structuring the first global circuit 260a in a source follower, settling performance of the column source-follower buffer 244 can be improved.

Furthermore, according to the second embodiment of the present disclosure, by structuring the first global circuit 260a in a source follower, the linearity can be maintained even when the input capacitance of the A/D converter 27 is increased.

Moreover, according to the second embodiment of the present disclosure, because the reference-signal generating unit 26c generates a reference signal having a fluctuation component in phase with an imaging signal that is generated by the pixel 230, it is possible to convert the imaging signal into a digital imaging signal to be output, in a condition practically not influenced by a common mode noise.

Furthermore, according to the second embodiment of the present disclosure, because a capacitor connected to the input terminal of the comparator circuit 403 can be made substantially flat, it is possible to prevent degradation of the linearity of an output signal that is output by the A/D converter 27.

Third Embodiment

Next, a third embodiment of the present disclosure is described. The third embodiment differs in a configuration of the first A/D converting unit 280 and the second A/D converting unit 290 in the A/D converter 27 according to the first embodiment. In the following, configurations of a first A/D converting unit and a second A/D converting unit are described. Note that like reference symbols are assigned to like components as the endoscope system 1 according to the first embodiment described above, and description thereof is omitted.

Configuration of First A/D Converting Unit

Figure 17:
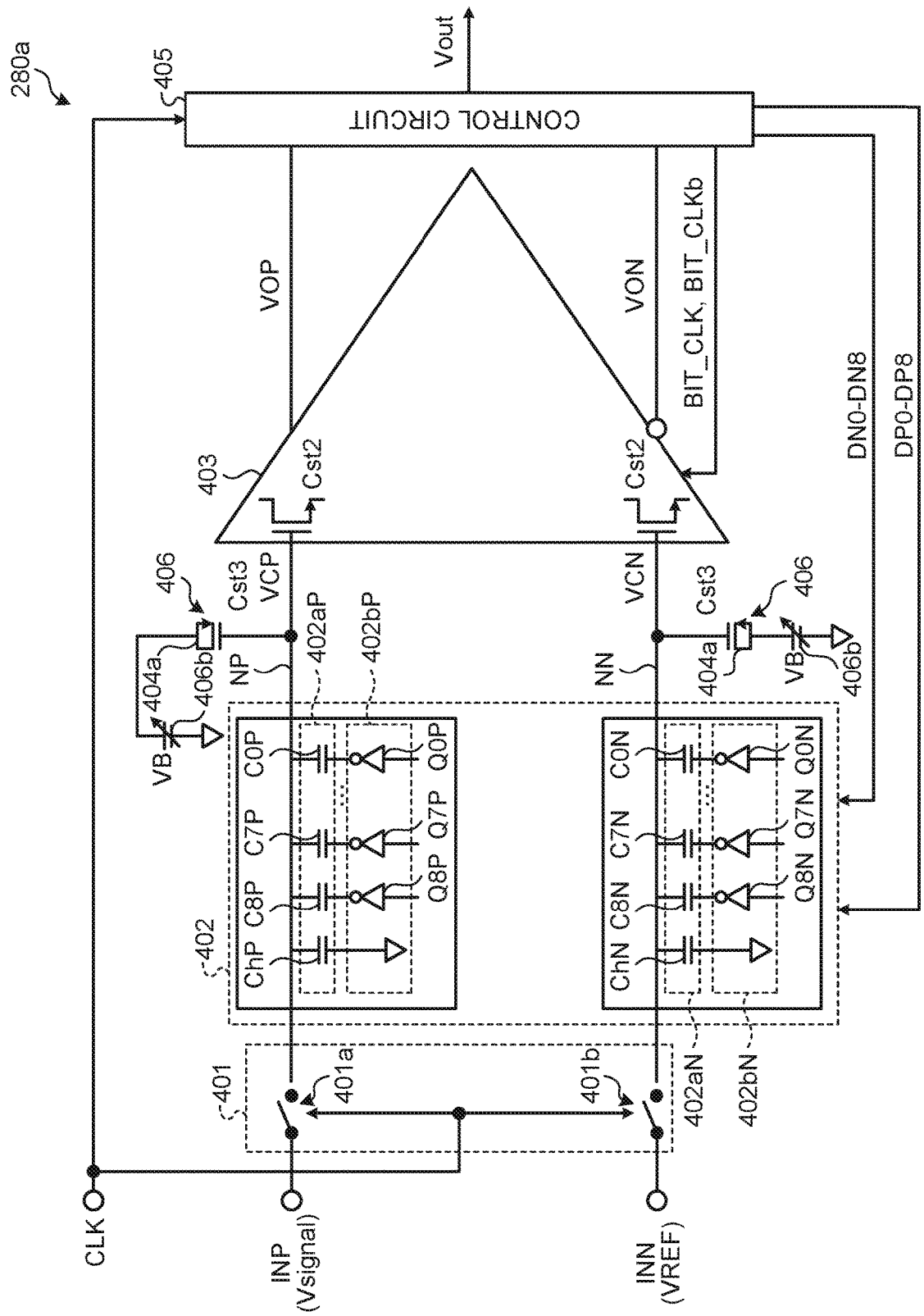
FIG. 17 is a circuit diagram schematically illustrating a configuration of a first A/D converting unit according to a third embodiment of the present disclosure.

FIG. 17 is a circuit diagram schematically illustrating a configuration of the first A/D converting unit according to the third embodiment. Because the first A/D converting unit and the second A/D converting unit according to the third embodiment have the same circuit configuration, only the configuration of the first A/D converting unit is described in the following, and description of the configuration of the second A/D converting unit is omitted. Moreover, a first A/D converting unit 280a illustrated in FIG. 17 is a successive approximation A/D converter and is an A/D converter of 9-bit output, but not limited thereto, the number of output bit may be changed as appropriate.

The first A/D converting unit 280a illustrated in FIG. 17 includes a correction circuit 406 in place of the correction circuit 404 of the first A/D converting unit 280 according to the first embodiment described above.

The correction circuit 406 cancels a stray capacitance of the input transistor of the comparator circuit 403, and thereby corrects a pair of analog signals input to the comparator circuit 403. The correction circuit 406 includes the correction transistor 404a that cancels a stray capacitance of the input transistor of the comparator circuit 403, and a bias circuit 406b that applies the bias voltage VB to the correction transistor 404a, and that can adjust the bias voltage VB. The bias circuit 406b is configured using, for example, a variable resistor, or the like. The bias circuit 406b may be configured using an output signal of the DAC circuit.

Method of Adjusting Bias Voltage VB of Correction Circuit

Figure 18:
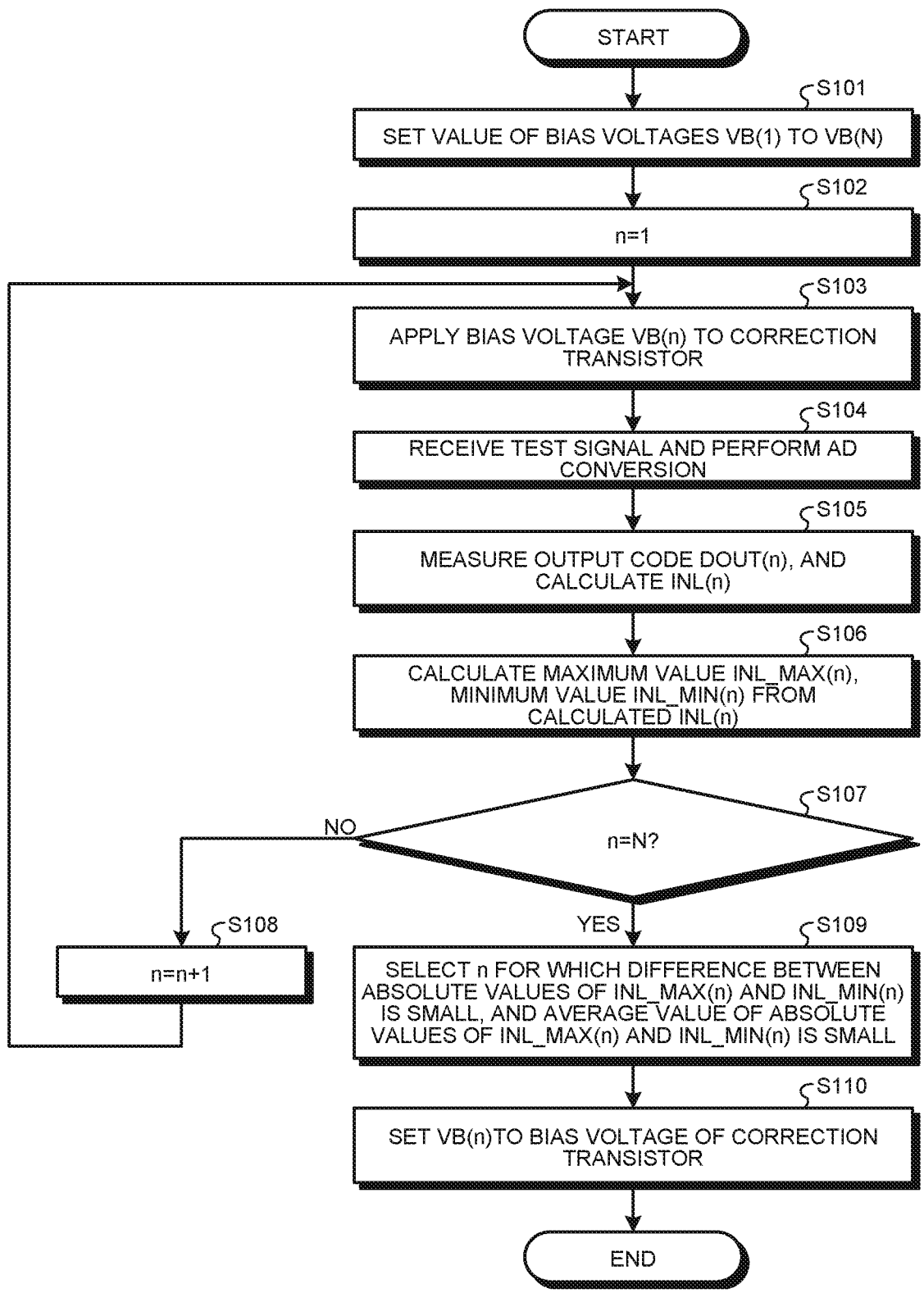
FIG. 18 is a flowchart illustrating a method of adjusting a bias voltage of a correction circuit according to the third embodiment of the present disclosure.
Figure 19A:
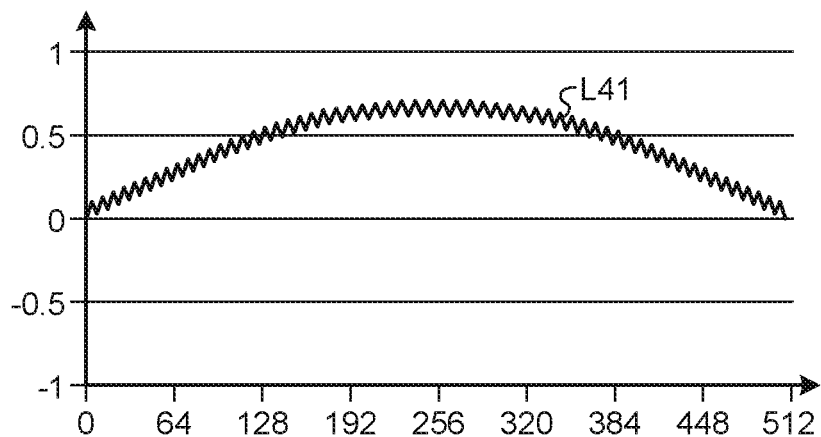
FIG. 19A is a diagram schematically illustrating INL characteristics when the bias voltage (1) of the correction circuit according to the third embodiment of the present disclosure is changed.
Figure 19B:
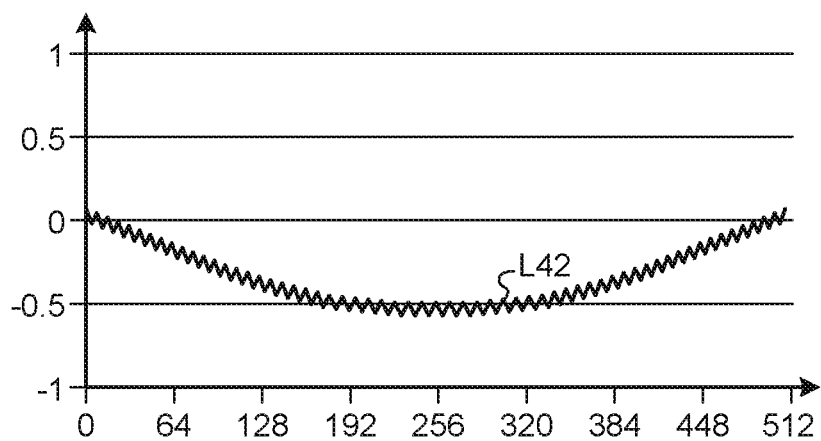
FIG. 19B is a diagram schematically illustrating the INL characteristics when a bias voltage (N) of the correction circuit according to the third embodiment of the present disclosure is changed.
Figure 19C:
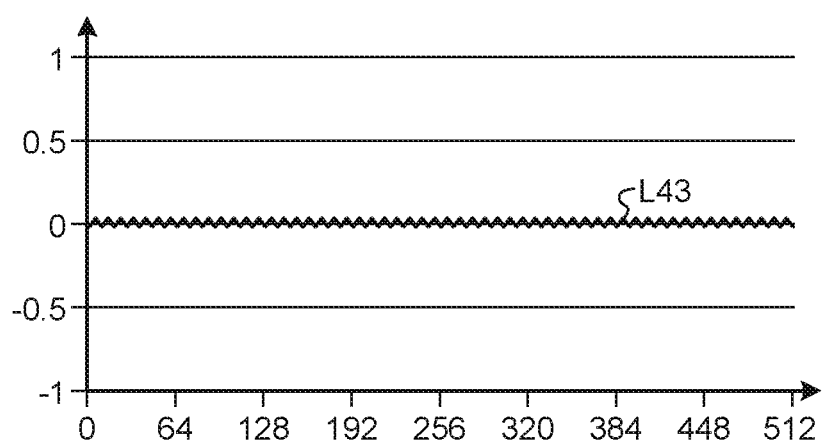
FIG. 19C is a diagram schematically illustrating the INL characteristics when a bias voltage (n) of the correction circuit according to the third embodiment of the present disclosure is changed.

Next, a method of adjusting a bias voltage of the correction circuit 406 illustrated in FIG. 17 is described. FIG. 18 is a flowchart illustrating a method of adjusting a bias voltage of the correction circuit 406. FIG. 19A to FIG. 19C are diagrams schematically illustrating an INL characteristic (9-bit ADC) when the bias voltage (n) of the correction circuit 406 is changed. In FIG. 19A to FIG. 19C, a horizontal axis represents code, and a vertical axis represents INL[a.u]. Moreover, a curve L41 in FIG. 19A represents an INL characteristic of bias voltage VB=VB(1), a curve L42 in FIG. 19B represents an INL characteristic of bias voltage VB=Vb(N), and a curve L43 in FIG. 19C represents an INL characteristic of bias voltage VB=VB(n).

As illustrated in FIG. 18, first, the user adjusts the bias circuit 406b and sets a value of the bias voltage VB(1) to VB(N) (step S101), and sets n=1 (step S102). N represents the maximum value when the bias voltage VB is divided.

Subsequently, the bias circuit 406b applies the bias voltage VB(n) to the correction transistor 404a (step S103).

Thereafter, the user inputs a test signal to the first A/D converting unit 280a to cause A/D conversion (step S104), measures an output code DOUT(n) that is output from the first A/D converting unit 280a, to calculate INL(n) (step S105). In this case, the INL characteristic of the bias voltage VB(1) forms an upward convex shape as shown in the curve L41 in FIG. 19A.

Subsequently, the user calculates, from the calculated INL(n), the maximum value INL_MAX(n) of INL and the minimum value INL_MIN(n) (step S106).

Thereafter, the user determines whether n is N (step S107). When n is N (step S107: YES), it shifts to step S109 described later.

On the other hand, when n is not N (step S107: NO), the user increments n to (n=n+1) (step S108), and returning to step S103, steps S102 to S107 described above are repeated unit n=N is obtained. In this case, the INL characteristic of the bias voltage VB(N) forms a downward convex shape as shown in the curve L42 in FIG. 19B.

At step S109, the user selects n for which a difference between absolute values of the maximum value INL_MAX(n) and the minimum value INL_MIN(n) is small, and an average value of absolute values of the maximum value INL_MAX(n) and the minimum INL_MIN(n) is small.

Thereafter, the user sets the bias voltage VB(n) as a bias voltage of the correction transistor 404a (step S110). Specifically, the user adjusts such that the bias voltage applied to the correction transistor 404a by the bias circuit 406b is to be VB(n). In this case, as illustrated in FIG. 19C, the INL characteristic of the bias voltage VB(n) forms a substantially straight line as shown in the curve L43 in FIG. 19C. After step S110, the user ends this processing.

According to the third embodiment of the present disclosure described above, because a capacitor connected to the input terminal of the comparator circuit 403 can be made substantially flat, it is possible to prevent degradation of the linearity of an output signal that is output by the A/D converter 27.

Other Embodiments

In the embodiments of the present disclosure, an imaging signal generated by an imaging device is transmitted to a processor through a transmission cable, but it does not need to be wired transmission, for example, and it may be wireless communication. In this case, the imaging signal can be transmitted to the processor by a predetermined wireless communication standard (for example, Wi-Fi (registered trademark) or Bluetooth (registered trademark)). The wireless communication may be performed also by other wireless communication standards, of course. Furthermore, besides the imaging signal, update information to update various kinds of information of an endoscope may be transmitted.

Moreover, in the embodiments of the present disclosure, an imaging device is configured in one chip. However, two chips may be used. In this case, one is a pixel chip in which multiple pixels are arranged and the other is a circuit chip in which various kinds of circuits from a reading unit to an A/D converter are arranged. Additionally, the circuit chip may be stacked on the pixel chip.

Furthermore, in the embodiment of the present disclosure, a digital imaging signal is transmitted to the connector unit from the A/D converter through a transmission cable, but by arranging, for example, an optical coupler that converts the digital imaging signal into an optical signal, or the like, the digital imaging signal may be transmitted to the connector unit as the optical signal.

Moreover, in the present application, operations have been described using terms of "first", "next", "subsequently", "thereafter", and the like for convenience in description of the flowchart of various operations described above, but it is not intended that the operations are required to be performed in this order.

Furthermore, in the embodiments of the present disclosure, the processor and the light source device are formed in one piece, but not limited thereto, for example, the processor and the light source device may be arranged separately.

Moreover, the embodiments of the present disclosure have been described using a simultaneous endoscope as an example, but it is applicable also to a frame sequential endoscope.

Furthermore, the embodiments of the present disclosure are applicable not only to a soft endoscope (vertical endoscope), but also to a hard endoscope, a sinus endoscope, and an endoscope system including an electrosurgical knife and an inspection probe, and the like.

Furthermore, the embodiments of the present disclosure have been described using an imaging device of an endoscope in which a successive approximation A/D converter is arranged at a distal end of an insertion portion to be inserted into a subject as an imaging device as an example, but it is not limited thereto. It is applicable to an imaging device in which a lens unit is detachable, an imaging device in which mobile phone is integrated, an imaging device without a display monitor, a surveillance camera operated through a network, an imaging device used for a digital camcorder and a microscope.

Moreover, the present disclosure is not limited to the embodiments and the modifications described above as they are. In a practical phase, it can be implemented by changing components within a range not departing from the gist of the disclosure. Furthermore, by combining the components disclosed in the embodiments described above, various disclosures can be formed. For example, some of the components out of all of the components described in the embodiments and the modifications described above can be deleted. Moreover, the components described in the embodiments and the modifications can be combined as appropriate.

Furthermore, a term that is described with a different broader or synonymous term at least once in the specification of in the drawings can be replaced with the different term in any part of the specification or the drawings. As described, various modifications and applications are enabled within a range not departing from the gist of the disclosure.

According to the present disclosure, an effect of preventing degradation of linearity of an output signal is obtained.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:
1. A successive approximation analog-to-digital converter comprising;
   a sampling circuit configured to sample a pair of analog signals input as a differential input signal;
   a capacitor circuit that has a binary capacitance configured to hold the pair of analog signals sampled by the sampling circuit, the capacitor circuit being configured to reflect a signal level of a reference signal to the pair of analog signals through the binary capacitance to generate a pair of voltage signals;
   a comparator circuit that includes an input transistor to which the pair of voltage signals are input, the comparator circuit being configured to compare one of the pair of voltage signals with the other signal of the pair of voltage signals;
   a correction circuit that is provided in a previous stage to the comparator circuit, the correction circuit being configured to output the pair of voltage signals in which voltage dependency of stray capacitance in the input transistor is cancelled to the comparator circuit; and
   a control circuit configured to successively determine a value of each bit of a digital signal corresponding to the binary capacitance based on a comparison result by the comparison circuit, and to reflect the value of each bit of the digital signal to the reference signal.

2. The successive approximation analog-to-digital converter according to claim 1, wherein
   the correction circuit includes a correction transistor configured to cancel the voltage dependency of the stray capacitance; and
   a bias circuit configured to apply a predetermined bias voltage to the correction transistor.

3. The successive approximation analog-to-digital converter according to claim 2, wherein
   the bias circuit is configured to adjust the bias voltage.

4. The successive approximation analog-to-digital converter according to claim 3, wherein
   a voltage dependence of a capacitance of the correction transistor is inverse to a voltage dependence of the stray capacitance.

5. An imaging device comprising:
   the successive approximation analog-to-digital converter according to claim 1;
   an imaging device including a plurality of pixels that are arranged in a two-dimensional matrix, and that receive light input from outside to perform photoelectric conversion, and that outputs an imaging signal, wherein
   the imaging device includes
   a noise removing circuit that is arranged for each of columns of the two-dimensional matrix in which the pixels are arranged, the noise removing circuit being configured to remove a noise component included in the imaging signal;
   a plurality of column source-follower buffers that are arranged for each of the columns of the two-dimensional matrix in which the pixels are arranged, the plurality of column source-follower buffers being configured to and that amplify the imaging signal from which the noise component is removed by the noise removing unit;
   a column selecting circuit that sequentially selects the column source-follower buffers to output the imaging signal; and
   a buffer circuit that forms a voltage follower circuit, being connected to the column source-follower buffer sequentially selected by the column selecting circuit, and that subjects a voltage of the imaging signal output from the column source-follower buffer to impedance transformation, to output to the successive approximation analog-to-digital converter.

6. The imaging device according to claim 5, wherein
the imaging device further includes
   a reference-signal generating circuit that generates a reference signal including a fluctuation component in phase with the signal generated by the pixel, to output to the successive approximation analog-to-digital converter, and
the successive approximation analog-to-digital converter accepts the imaging signal and the reference signal as the differential input signal.

7. The imaging device according to claim 6, wherein
the reference-signal generating circuit includes any one of a device and a circuit having a structure equivalent to the pixel.

8. An endoscope comprising:
an imaging device according to claim 5; and
an insertion portion insertable to a subject, the insertion portion includes the imaging device at a distal end.

9. A setting method that is performed in a successive approximation analog-to-digital converter having
   a correction circuit that includes a sampling circuit that samples a pair of analog signals input as a differential input signal; a capacitor circuit that has a binary capacitance holding the pair of analog signals sampled by the sampling circuit, the capacitor circuit being configured to reflect a signal level of a reference signal to the pair of analog signals through the binary capacitance to generate a pair of voltage signals; a comparator circuit that includes an input transistor to which the pair of voltage signals are input, the comparator circuit being configured to compare one of the pair of voltage signals with the other signal of the pair of voltage signals; a correction transistor that is provided in a previous stage to the comparator circuit, the correction transistor being configured to cancel voltage dependency of stray capacitance in the input transistor; and a bias circuit that applies a predetermined bias voltage to the correction transistor, the correction circuit being configured to output the pair of voltage signals to the comparator circuit; and
a control circuit configured to successively determine a value of each bit of a digital signal corresponding to the binary capacitance by binary search, based on a comparison result by the comparator circuit, and to reflect the value of each bit of the digital signal to the reference signal, the method comprising:

setting a value of the bias voltage applied by the bias circuit;

applying the bias voltage having the set value sequentially to the correction transistor;

inputting a test signal to the successive approximation analog-to-digital converter sequentially such that the successive approximation analog-to-digital converter is caused to perform analog-to-digital conversion;

calculating an integral non-linearity difference of each of the output code based on a measurement result obtained by sequentially measuring the output code converted at the analog-to-digital conversion;

calculating respective maximum value and minimum value of the integral non-linearity difference for each of the output code, based on the integral non-linearity difference; and setting a value of the bias voltage such that a difference between absolute values of the calculated maximum values and the calculated minimum values is reduced, and such that an average value of the absolute values of the maximum values and the minimum values is reduced, as a value of the bias voltage to be applied by the bias circuit.

* * * * *